(12) United States Patent
Levendowski et al.

(10) Patent No.: US 6,381,481 B1
(45) Date of Patent: Apr. 30, 2002

(54) PORTABLE EEG ELECTRODE LOCATOR HEADGEAR

(75) Inventors: Daniel J. Levendowski; Christine Berka, both of Carlsbad; Zoran R. Konstantinovic, Vista, all of CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 0 days.

(21) Appl. No.: 09/492,380

(22) Filed: Jan. 27, 2000

Related U.S. Application Data

(63) Continuation-in-part of application No. 09/245,784, filed on Feb. 5, 1999, now Pat. No. 6,161,030.

(51) Int. Cl.⁷ .............................................. A61B 5/0478
(52) U.S. Cl. ........................ 600/383; 600/393; 607/139
(58) Field of Search ................................. 600/383, 390, 600/393, 544; 602/139

(56) References Cited

U.S. PATENT DOCUMENTS

| | | | |
|---|---|---|---|
| 3,490,439 A | 1/1970 | Rolston | 600/383 |
| 3,623,477 A | * 11/1971 | Trent | 600/383 |
| 3,998,213 A | 12/1976 | Price | |
| 4,537,198 A | 8/1985 | Corbett | |
| 4,709,702 A | 12/1987 | Sherwin | |
| 4,770,180 A | 9/1988 | Schmidt et al. | |
| 4,836,219 A | 6/1989 | Hobson et al. | |
| 4,967,038 A | 10/1990 | Gevins et al. | |
| 5,038,782 A | 8/1991 | Gevins et al. | |
| 5,273,037 A | 12/1993 | Itil et al. | |
| 5,291,888 A | 3/1994 | Tucker | |
| 5,293,867 A | 3/1994 | Oommen | 600/383 |
| 5,348,006 A | 9/1994 | Tucker | |
| 5,357,957 A | 10/1994 | Itil et al. | |
| 5,404,875 A | 4/1995 | Gevins et al. | |
| 5,479,934 A | 1/1996 | Imran | |
| 5,564,433 A | 10/1996 | Thornton | |
| 5,800,351 A | 9/1998 | Mann | 600/383 |

OTHER PUBLICATIONS

Article entitled "A Dry Electrode For EEG Recording,"p0 B. Taheri, R. Knight, and R. Smith, 1994 Elsevier Science Ireland Ltd. pp. 2–9.

\* cited by examiner

*Primary Examiner*—Lee Cohen
(74) *Attorney, Agent, or Firm*—Fulwider Patton Lee & Utecht, LLP

(57) ABSTRACT

The EEG electrode locator headgear allows the user to locate and apply disposable EEG electrodes accurately according to the International 10/20 System without technical assistance, to allow the acquisition of high quality EEG signals. The headgear includes a front forehead pad, a base strap assembly connected to the front forehead pad, a plurality of EEG electrode locators for receiving EEG electrodes, and a plurality of locator straps connected to the front pad of material, the base strap assembly, and to the plurality of EEG electrode locators for accurately positioning the plurality of EEG electrode locators positioned relative to the scalp of a user. A visor can be attached to the front pad of material, and the base strap assembly may include an occipital locator device. A plunger assembly with spreadable fingers for optionally parting the hair of the user's scalp is also provided that is inserted in the electrode locators to optionally prepare the user's scalp and to seat the electrodes. In one embodiment, a spreader portion of the plunger assembly is formed of electrically conductive material, such as electrically conductive silicone. An elastic, stretchable cap portion may also be connected to the EEG electrode locators, for biasing the plurality of electrode locators toward the user's scalp.

83 Claims, 14 Drawing Sheets

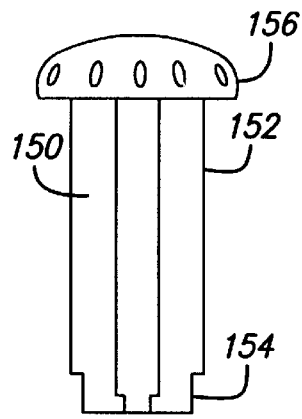 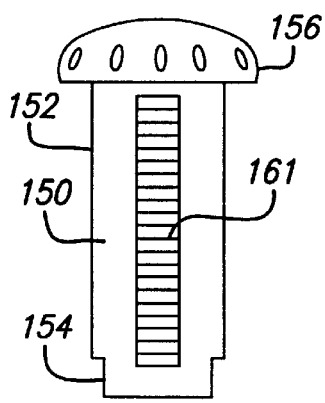 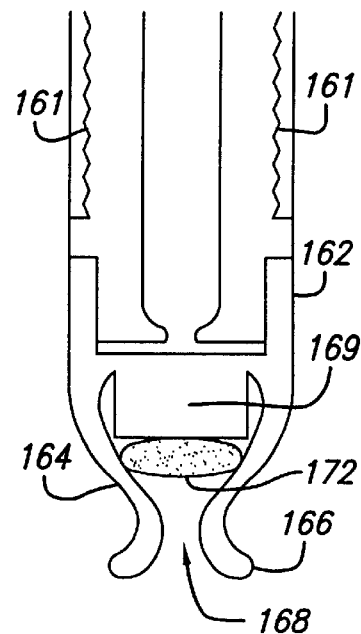
FIG. 13  FIG. 14  FIG. 15
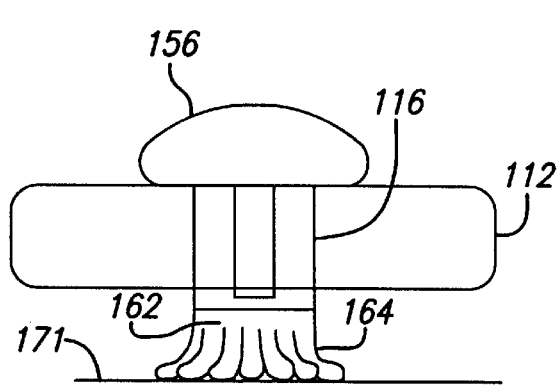 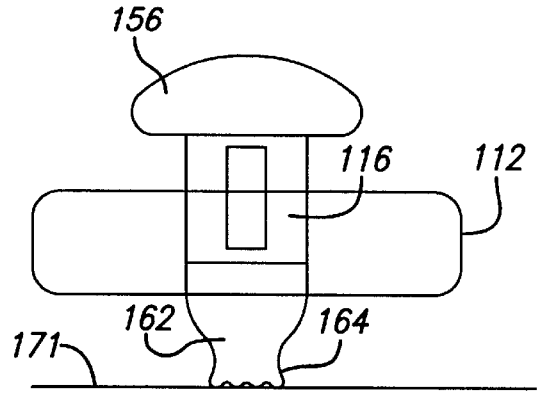
FIG. 16  FIG. 17

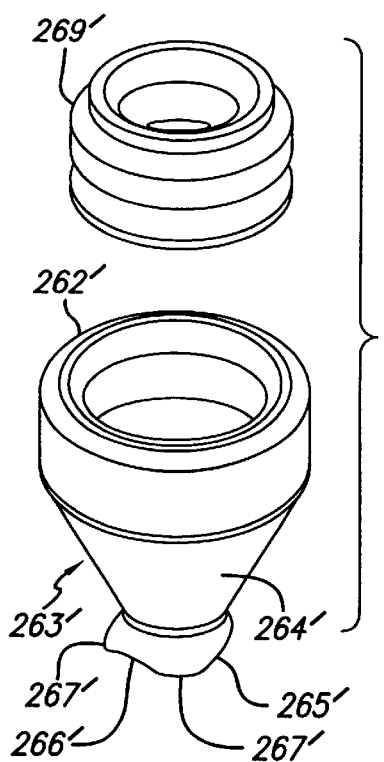
FIG. 24
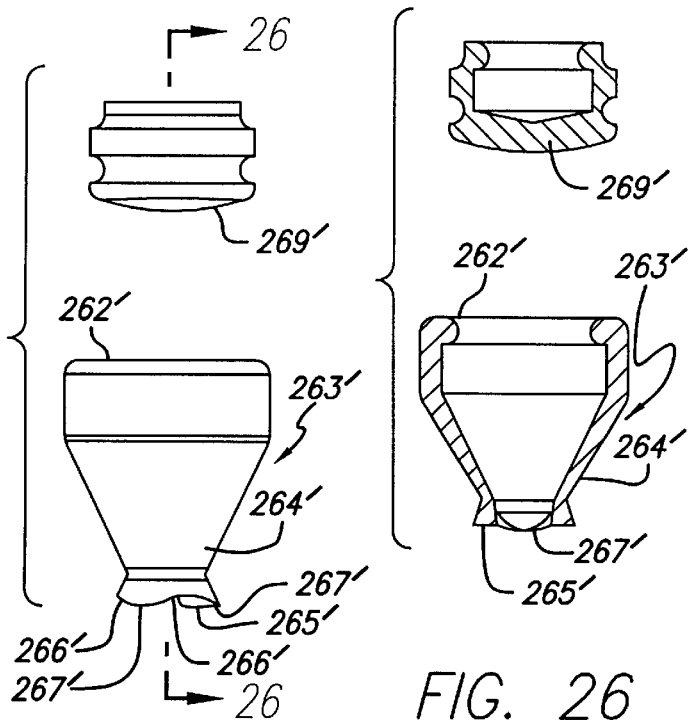
FIG. 25
FIG. 26
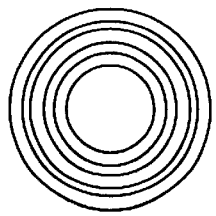
FIG. 27
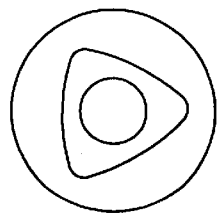
FIG. 28

PORTABLE EEG ELECTRODE LOCATOR HEADGEAR

RELATED APPLICATIONS

This is a continuation in part of Ser. No. 09/245,784 filed Feb. 5, 1999, now U.S. Pat. No. 6,161,030.

GOVERNMENT LICENSE RIGHTS

The United States Government has rights in this invention pursuant to research supported in the whole or in part by NIH Contracts R43-NS-62344, N43-NS-72367 and N44-NS-72367 and grants R43-NS-35387, R44-NS-35387 and R44-NS38036 awarded by the National Institute of Neurological Disorders and Stroke.

BACKGROUND OF THE INVENTION

1. Field of the Invention

This invention relates generally to devices for the acquisition of electroencephalographic (EEG) signals, and more particularly concerns an electrode locator device that can be applied by a user without assistance for acquiring high quality EEG signals, and is comfortable and cosmetically acceptable for use during daily activities.

2. Description of Related Art

Advances in detection and characterization of electroencephalographic (EEG) signals from the brain have allowed EEG monitoring to be useful in analysis of neurological disorders, and laboratory studies of awareness and sleep. Recent advances have, for example, provided much information about the correlation between EEG signals and an individual's level of arousal, in a continuum from vigilance to drowsiness, and sleep onset. Devices for monitoring EEG signals are typically used in a laboratory environment or in a home for sleep studies, but are typically set up and operated by trained technicians. Shifts in EEG signals have been directly correlated with changes in performance, particularly during tasks which require sustained attention over prolonged periods of time. However, application of EEG monitoring to environments for study and monitoring of brain performance, such as for monitoring brain activity in the home, office, aircraft cockpit, and train or truck operations cabins, for example, has been severely hampered by cumbersome detection and recording equipment, and the need for the assistance of a technician typically required to obtain high quality data.

In fitting EEG electrodes to the scalp of a subject being monitored, an EEG technician will typically first measure the distances between the nasium and the occipital bone, and between the mastoid processes, to identify the top center (Cz) of the head, and will then position all other electrodes relative to these landmarks to comply with the International 10/20 System that is well known in the art as the standard for positioning of EEG electrodes. The technician will then part the hair of the scalp of the subject at the intended electrode sites, clean the electrode sites to remove dirt, hair oil, and the like, and prepare the scalp to remove the top layer of dead skin, to ensure that low scalp-electrode impedance values are obtained.

Conventionally, after preparation of the intended electrode sites on the scalp, electrodes are glued to the scalp with collodion, typically a viscous solution of pyroxilin, a commercially available nitrocellulose, in ether and alcohol, that is a particularly noxious preparation that can bond with the scalp and hair, to provide a stable scalp-electrode interface, until dissolved by a solvent such as acetone, or a non-acetone, oil based collodion remover.

A variety of hats, caps, helmets and headgear are known that have been developed to position EEG electrodes according to the International 10/20 System and provide a scalp-electrode interface without the use of an adhesive such as collodion. However, these types of devices are commonly uncomfortable and unacceptable for use during activities of work and daily living. One such sleep monitoring headgear utilizes a circumferential elastic headband to generate an electrode seating pressure for a single electrode located at the top center of the head of a subject. It has been found, however, that when such a circumferential elastic headband is utilized to seat multiple electrodes, the headband slides up and posteriorly on the forehead.

Such conventional hats, caps, helmets and headgear also typically make it difficult for a user to part the hair or abrade their scalp at the electrode site without assistance. Particularly where disposable electrodes are used that are not to be bonded to the scalp of the user to provide an electrode-scalp interface, the placement of an electrode over hair can increase the impedance between the electrode and scalp, causing significant signal artifacts if the hair slides or is pulled across the surface of the electrode while signals are being acquired. One such conventional device requires the technician to lift or turn a disposable electrode on its side after a conductive gel on the electrode has made contact with the hair of the scalp, in order to part the hair at the intended area of the scalp for placement of the electrode. Several systems used in the laboratory for non-ambulatory EEG monitoring dispense electrode gel to the electrode, but would make an EEG electrode locator headgear uncomfortably heavy and inconvenient for ambulatory use outside a laboratory environment. Another type of device utilizes sharp tipped metal points to penetrate the dead layer of skin. However, such sharp metal points can pose a medical danger due to the potential for infection, particularly with repeated abrasions, and the possibility of penetration of the skull if the device were to be struck accidentally during ambulatory activity, or other activities during daily living.

It would therefore be desirable to provide an EEG electrode locator headgear that utilizes electrode locators to identify electrode sites, and gives the user access for application of electrodes to the electrode sites, permitting conventional scalp preparation techniques, such as application of abrasion cream with a "Q-tip", for example, to be applied by the user without technical assistance. It would also be desirable to provide an EEG electrode locator headgear utilizing a device allowing a user the option of preparing an intended electrode site on the scalp by parting of the hair, prior to seating of the electrodes, and for placement of electrodes. While prior EEG electrode locating techniques typically required a technician to accurately locate electrodes, it would be desirable to provide an EEG electrode locator headgear that utilizes a locating device that can be positioned by the user over a prominent location on the scalp of the user, such as over the occipital bone, or over the nasium, to orient the headgear and confirm accurate placement of the EEG electrodes. The present invention meets these needs.

SUMMARY OF THE INVENTION

Briefly, and in general terms, the present invention provides for an EEG electrode locator headgear for a user that allows the user to locate and apply disposable EEG electrodes accurately according to the International 10/20 System without technical assistance, to allow the acquisition of high quality EEG signals. The EEG electrode locator headgear is portable and comfortable, allowing it to be worn by the user during daily activities as one would a cap or visor. The headgear provides a stable electrode-scalp interface for a plurality of electrodes without covering the entire head, and without requiring a chin strap for normal adult usage, and allows the hair to be parted and optionally preparation of the scalp by the user without technical assistance.

The invention accordingly provides for an electroencephalograph (EEG) electrode locator headgear including a front pad of material having first and second ends, the front pad of material being adapted to extend across a user's forehead, a base strap assembly having a first end connected to the first end of the front pad of material, and a second end connected to the second end of the front pad of material, the front pad of material and the base strap assembly being adapted to be secured comfortably around the circumference of a user's head, a plurality of EEG electrode locators adapted to receive EEG electrodes, and a plurality of locator straps connected to the front pad of material, the base strap assembly, and to the plurality of EEG electrode locators for accurately positioning the plurality of EEG electrode locators positioned relative to the scalp of a user.

In a presently preferred embodiment, the front pad of material includes a visor or front bill attached to the front pad of material, which is typically non-elastic. The base strap assembly is preferably adjustable, and in a presently preferred aspect comprises a pair of adjustable elastic straps connected at one end to the front pad of material and adjustably connected together at the other end. The base strap may also advantageously include an occipital locator device adapted to be seated on a region of the user's scalp over the user's occipital bone, with the base strap assembly including first and second elastic edge straps connected at one end to the front pad of material, and adjustably connected at the other end to the occipital locator device. The occipital locator device preferably has a plurality of feet adapted to be positioned over the user's occipital bone. In an alternative preferred embodiment, an anterior locator strap having a free end adapted to be positioned over the user's nasium can be connected to the front pad of material, to allow the user to confirm accurate placement of the electrode locators.

In another presently preferred aspect of the invention, the EEG electrode locators each comprise a hollow tubular base adapted to receive an EEG electrode, and an annular flange extending from an upper edge of the hollow tubular base, with the annular flange including a plurality of slots for receiving a plurality of the locator straps. In another presently preferred aspect, the hollow tubular base includes an EEG electrode locator electrical conductor adapted to be electrically connected to an EEG electrode inserted in the hollow tubular base of the EEG electrode locator, and intermediate electrical conductors are electrically connected to the EEG electrode locator electrical conductors and are adapted to be connected to an EEG monitor. In a presently preferred embodiment, three EEG electrode locators are provided, adapted to be positioned at a central (Cz) position, a parietal (Pz) position, and an occipital (Oz) position, relative to the scalp of a user. Alternatively, additional electrode locators may be provided for positioning additional electrodes according to the International 10/20 system.

In another presently preferred aspect of the invention, the plurality of locator straps are made of elastic material, such that the locator straps bias the plurality of EEG electrode locators, and thereby the electrodes inserted into the electrode locators, with a biasing pressure toward the user's scalp, to provide a stable electrode-scalp interface capable of producing a high signal quality. A plurality of electrodes are also provided that are adapted to be seated in the plurality of electrode locators, respectively. As noted above, at least three electrodes are provided, although the electrode headgear can be adapted to accept more or fewer than three EEG electrodes, as desired. The electrodes are preferably disposable.

A plunger assembly is also preferably provided that is adapted to cooperate with the plurality of electrode locators either prior to or in conjunction with insertion of the EEG electrodes. The plunger assembly includes a hollow tubular base having an upper portion and a lower portion, and a plunger adapted to be received in the hollow tubular base. The plunger assembly is adapted to be inserted in the electrode locators to prepare the scalp of the user and to seat the electrodes.

The lower portion of the hollow tubular base advantageously includes a plurality of flexible, resilient fingers having distal ends that are biased to meet at a common distal central location, and that can be spread in order to part the hair of the scalp of the user at a desired site on the scalp of the user in preparation of the site for receiving an EEG electrode. The flexible, resilient fingers on the hollow tubular base of the plunger assembly are presently preferably plastic. The distal flexible, resilient fingers of the plunger hollow tubular base can be spread by insertion of an electrode through the plunger hollow tubular base, so that the plunger assembly can be used to simultaneously part the hair by spreading of the distal fingers of the plunger hollow tubular base, and seat the disposable electrode, and optionally also may be used to abrade the scalp of the user at the intended location of the electrode, such as by manually twisting the hollow tubular base to rub the distal ends of the distal fingers against the scalp of the user. The plunger is adapted to be inserted in the hollow tubular base of the plunger assembly to spread the distal flexible, resilient fingers.

In one presently preferred alternate embodiment, the plunger has an external helical rib, and the hollow tubular base has a corresponding interior groove for receiving and guiding the external helical rib of the plunger as the plunger is inserted in the hollow tubular base of the plunger assembly, to provide a predetermined turning and torque to the plunger as it is inserted. In another presently preferred aspect, the hollow tubular base of the plunger assembly includes an electrical conductor adapted to be electrically connected between an electrode inserted in the hollow tubular base and one of the electrode locators for conducting EEG signals from the electrodes to an EEG monitor.

In a second preferred embodiment, the invention provides for an electroencephalograph (EEG) electrode locator headgear comprising a base strap assembly adapted to be secured comfortably around the circumference of a user's head, an elastic, stretchable cap portion connected to the plurality of EEG electrode locators, and a plurality of EEG electrode locators mounted to the elastic, stretchable cap portion for accurately positioning the plurality of EEG electrode locators relative to the user's scalp, and for biasing the plurality of electrode locators toward the user's scalp. A plurality of EEG electrodes are also provided that are adapted to be received in and cooperate with the plurality of EEG electrode locators, respectively. Each of the EEG electrodes includes a plunger assembly adapted to optionally prepare the user's scalp and to seat the electrode in one of the EEG electrode locators. The plunger assembly includes a plunger member having an electrically conductive spreader member mounted to the lower end of the plunger member, and the spreader member advantageously includes a plurality of flexible, resilient fingers having distal ends biased to meet at a common distal central location. The plunger assembly preferably comprises an electrical conductor mounted to the plunger member adapted and electrically connected between the electrically conductive spreader member and the EEG electrode locator for conducting EEG signals from the electrodes to an EEG monitor. The flexible, resilient fingers are adapted to spread apart by exertion of downward pressure of the plunger assembly against the user's scalp, so as to part the hair of the user's scalp, for preparation of the scalp for effective contact by the electrodes. The plunger is preferably adapted to be inserted in the electrode locator to spread the distal flexible, resilient fingers, and the plunger assembly can be used to abrade the users scalp at the intended location of the electrode by manually twisting the plunger assembly to rub the distal ends of the distal fingers against the user's scalp. In one presently preferred aspect, the plunger assembly comprises a cap connected to the upper portion of the plunger member. In order to improve the comfort of the user in applying the electrodes to the user's scalp, the spreader member preferably comprises an electrically conductive cushion portion located between the flexible, resilient fingers adapted to rest against the user's scalp after the electrode has been pressed downward to seat the electrode on the user's scalp and spread the flexible, resilient fingers, to cushion the pressure of the electrode on the user's scalp for additional comfort, and a conductive gel may also be disposed adjacent to the cushion portion of the spreader member and between the flexible, resilient fingers.

In a presently preferred aspect, the elastic, stretchable cap portion comprises one or more elastic locator straps connected to the plurality of EEG electrode locators, and preferably comprises a plurality of elastic locator straps, which can be made of elastic material, such as an elasticized fabric. The plurality of EEG electrode locators each comprise a plurality of slots for receiving the locator straps. In another presently preferred aspect, the elastic, stretchable cap portion comprises a stretch mesh cap of elastic, fabric material. An outer cap shell can optionally be further disposed over the elastic, stretchable cap portion, and may include shielding.

In another currently preferred aspect of the invention, the base strap assembly comprises a front pad of material adapted to extend across a user's forehead, and a visor or front bill of the headgear may also attached to the front pad of material. The base strap assembly is currently preferably adjustable, and in one presently preferred embodiment comprises a pair of adjustable elastic straps connected at one end to the front pad of material and adjustably connected together at the other end. The base strap assembly may also further comprise an occipital locator device adapted to be seated on a region of the user's scalp over the user's occipital bone.

In the second embodiment, each of the electrode locators preferably includes an electrical conductor adapted to be electrically connected to one of the EEG electrodes inserted in the electrode locator, and in a presently preferred aspect, the electrode locator electrical conductor comprises a plurality of electrically conductive spring connectors. In a preferred embodiment, a circuit board base member is mounted to the electrode locator electrical conductor, and the plurality of electrically conductive spring connectors are mounted to the circuit board base member. In another preferred aspect, the electrode locators include spring loaded detent pins for engagement with the electrode, and the plunger member preferably has a plurality of grooves or ratchet strips for engagement with the corresponding spring loaded detent pins for seating the plunger assembly in the electrode locators.

In another presently preferred aspect of the second embodiment, the EEG electrode locator headgear further comprises an operational pre-amplifier electrically connected to the electrode locator electrical conductor to receive EEG signals from the electrode, and the EEG signals from the electrode locators are conducted from the pre-amplifier to an analog to digital converter mounted on the EEG electrode locator headgear. An RF transmitter is preferably connected to receive output from the analog to digital converter, for communicating digital EEG signals to an apparatus for analyzing the digital EEG signals from the user, which preferably comprises a data processing unit for also providing feedback to the user. In a presently preferred aspect, the data processing unit is battery powered, and includes a speaker for transmitting audio alert messages to the user. In another presently preferred aspect, the RF transmitter of the EEG electrode locator headgear is a bi-directional RF transmitter-receiver for receiving feedback signals from the apparatus for analyzing the digital EEG signals from the user, and a speaker is mounted in the EEG electrode locator headgear for communicating audio messages from the data processing unit. Storage means may also be mounted in the EEG electrode locator headgear for storing audio messages in analog format. In another preferred aspect, the outer cap shell of the EEG electrode locator headgear includes a Faraday shield to shield the pre-amplifiers from external noise and artifacts which may result from the use of the RF transmitter.

These and other aspects and advantages of the invention will become apparent from the following detailed description and the accompanying drawings, which illustrate by way of example the features of the invention.

BRIEF DESCRIPTION OF THE DRAWINGS

FIG. 13 is a side elevational view of the EEG electrode plunger of FIG. 12;

FIG. 14 is a front view of the EEG electrode plunger of FIG. 12;

FIG. 15 is a partial sectional view of the EEG electrode plunger assembly of FIG. 12;

FIG. 16 is a sectional view of the EEG electrode plunger assembly of FIG. 12 inserted in an electrode locator prior to downward deployment of the EEG electrode plunger assembly onto the scalp of a user;

FIG. 17 is a sectional view of the EEG electrode plunger assembly of FIG. 12 inserted in an electrode locator following downward deployment of the EEG electrode plunger assembly onto the scalp of a user;

FIG. 24 is an exploded perspective view of another presently preferred embodiment of an electrically conductive spreader member of the EEG electrode plunger assembly of FIG. 18;

FIG. 25 is an exploded side elevational view of the electrically conductive spreader member of the EEG electrode plunger assembly of FIG. 24;

FIG. 26 is a sectional view of the electrically conductive spreader member of FIG. 25 taken along line 26—26;

FIG. 27 is a top plan view of the electrically conductive spreader member of the EEG electrode plunger assembly of FIG. 24;

FIG. 28 is a bottom plan view of the electrically conductive spreader member of the EEG electrode plunger assembly of FIG. 24;

DETAILED DESCRIPTION OF THE PREFERRED EMBODIMENTS

The application of EEG monitoring to common daily environments for study and monitoring of brain performance during the normal course of daily activities has been severely hampered by cumbersome detection and recording equipment, and the need for the assistance of a technician to set up and monitor the acquisition of data in order to obtain high quality data. Simply parting the hair of the scalp and preparation of the desired portions of the scalp of a subject for proper placement of electrodes has commonly required the assistance of a technician. Particularly when disposable electrodes are to be applied by a user that are not bonded to the scalp of the user to provide an electrode-scalp interface, the proper preparation and placement of an electrode over hair can be critical for obtaining high quality signal data.

Figure 1:
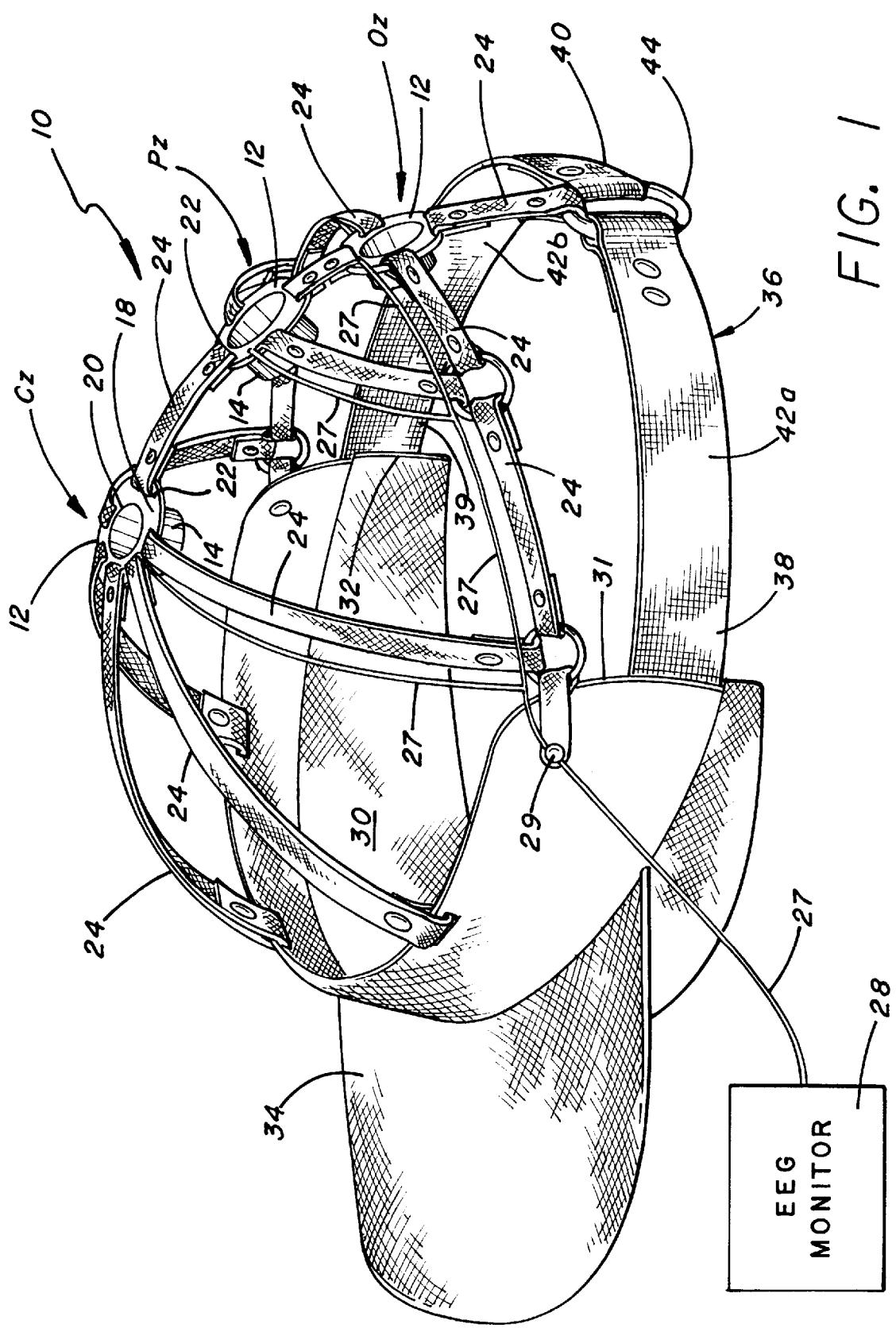
FIG. 1 is a top perspective view of a preferred embodiment of the EEG electrode locator headgear of the present invention.
Figure 4:
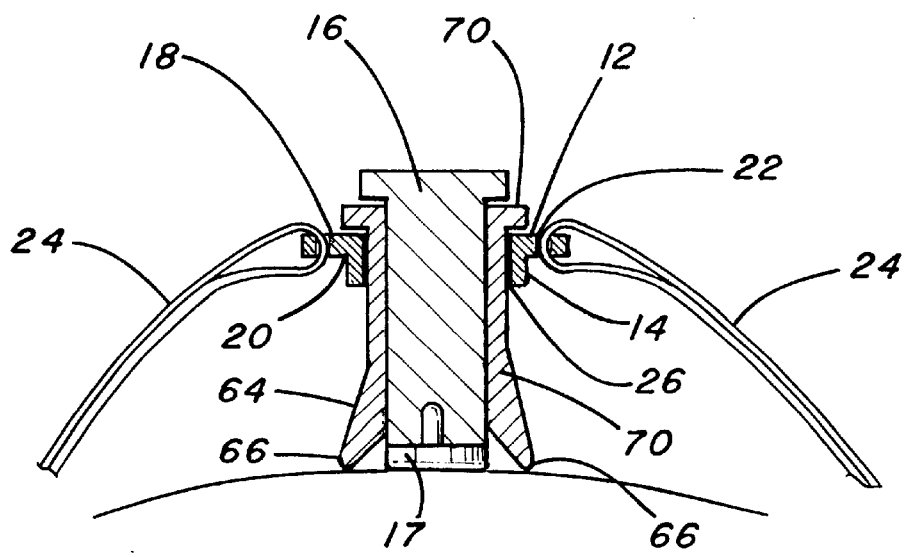
FIG. 4 is a cross-sectional view of the EEG electrode fully inserted in the plunger assembly and electrode locator of FIG. 3.
Figure 6:
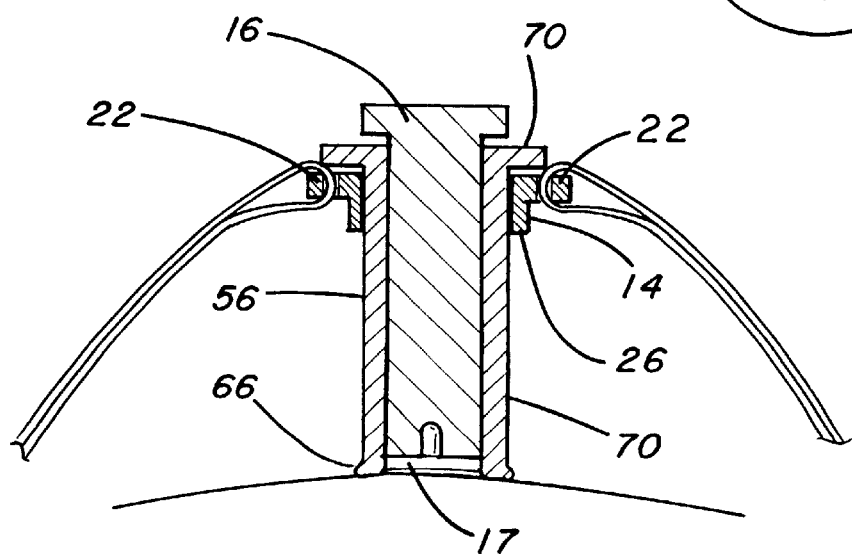
FIG. 6 is a cross-sectional view of an EEG electrode fully inserted in the plunger assembly and electrode locator of FIG. 5.
Figure 7:
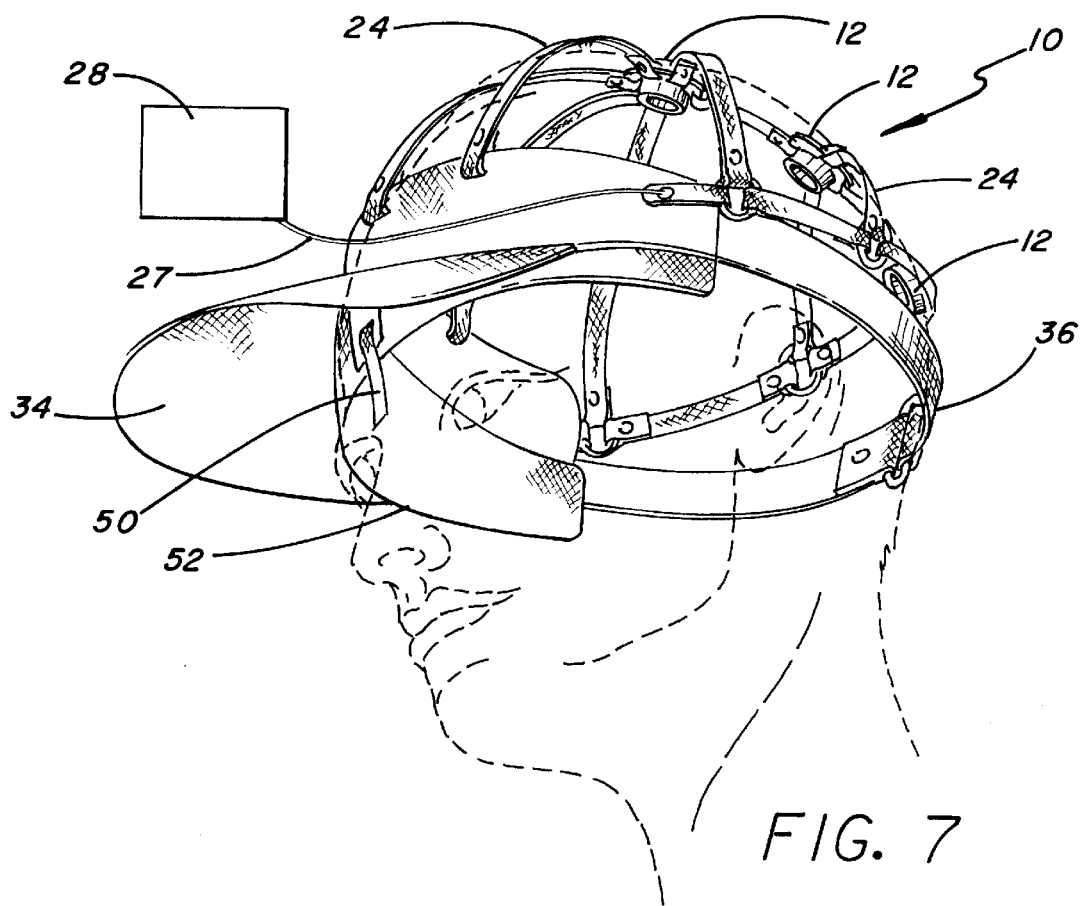
FIG. 7 is a bottom perspective view of an alternate embodiment of the EEG electrode locator headgear of the invention showing a front locator strap.

As is illustrated in the drawings, the invention is embodied in an electroencephalograph (EEG) electrode locator headgear that is portable and comfortable, and allows a user to locate and apply disposable EEG electrodes accurately according to the International 10/20 System without technical assistance, to allow the acquisition of high quality EEG signals. Referring to FIG. 1, the EEG electrode locator headgear 10 includes a plurality of EEG electrode locators 12 for receiving EEG electrodes for accurate positioning on the scalp of a user. The electrode locators each include a hollow tubular base 14 adapted to receive an EEG electrode plunger 16 and EEG electrode 17, as illustrated in FIGS. 4 and 6, and has an annular flange 18 extending from an upper edge 20 of the hollow tubular base. A plurality of electrodes are preferably provided, and are adapted to be seated in the corresponding plurality of electrode locators, respectively, by an interference or snap fit with the electrode locators, or by an interference or snap fit with a plunger assembly to be inserted in the electrode locators, as is further explained below. The annular flange typically includes a plurality of slots 22 for receiving a plurality of locator straps 24 that are currently preferably formed of elasticized fabric, in order to assist in biasing the electrode locators toward the scalp of the user, but non-elastic straps, such as fabric or nylon, for example, may also be suitable.

In a presently preferred embodiment, the hollow tubular base of the electrode locator includes an electrical conductor such as a conductor strip 26, shown in FIG. 4, adapted to be electrically connected to an EEG electrode, inserted in the hollow tubular base via a plunger assembly, or directly, as will be further explained below. Alternatively, the electrode locator can be made of an electrically conductive metal. The electrical conductor of the hollow tubular base is preferably adapted to be connected, such as by a cable 27 connectable to an electrically conductive connector 29 electrically connected to the electrode locators, to an EEG monitor 28 which is preferably a portable EEG monitor for ambulatory use, such as the portable EEG monitor disclosed in provisional application No. 60/114,528, filed Dec. 31, 1998, and non-provisional application No. 09/345,046 filed Jun. 30, 1999, which are incorporated herein by reference in their entirety. In a presently preferred embodiment, three EEG electrode locators are provided that are adapted to be positioned at the top central (Cz), parietal (Pz), and occipital (Oz) positions relative to the scalp of a user, although alternatively additional or fewer electrode locators may also be provided in the headgear for locating EEG electrodes according to the International 10/20 system.

Figure 2:
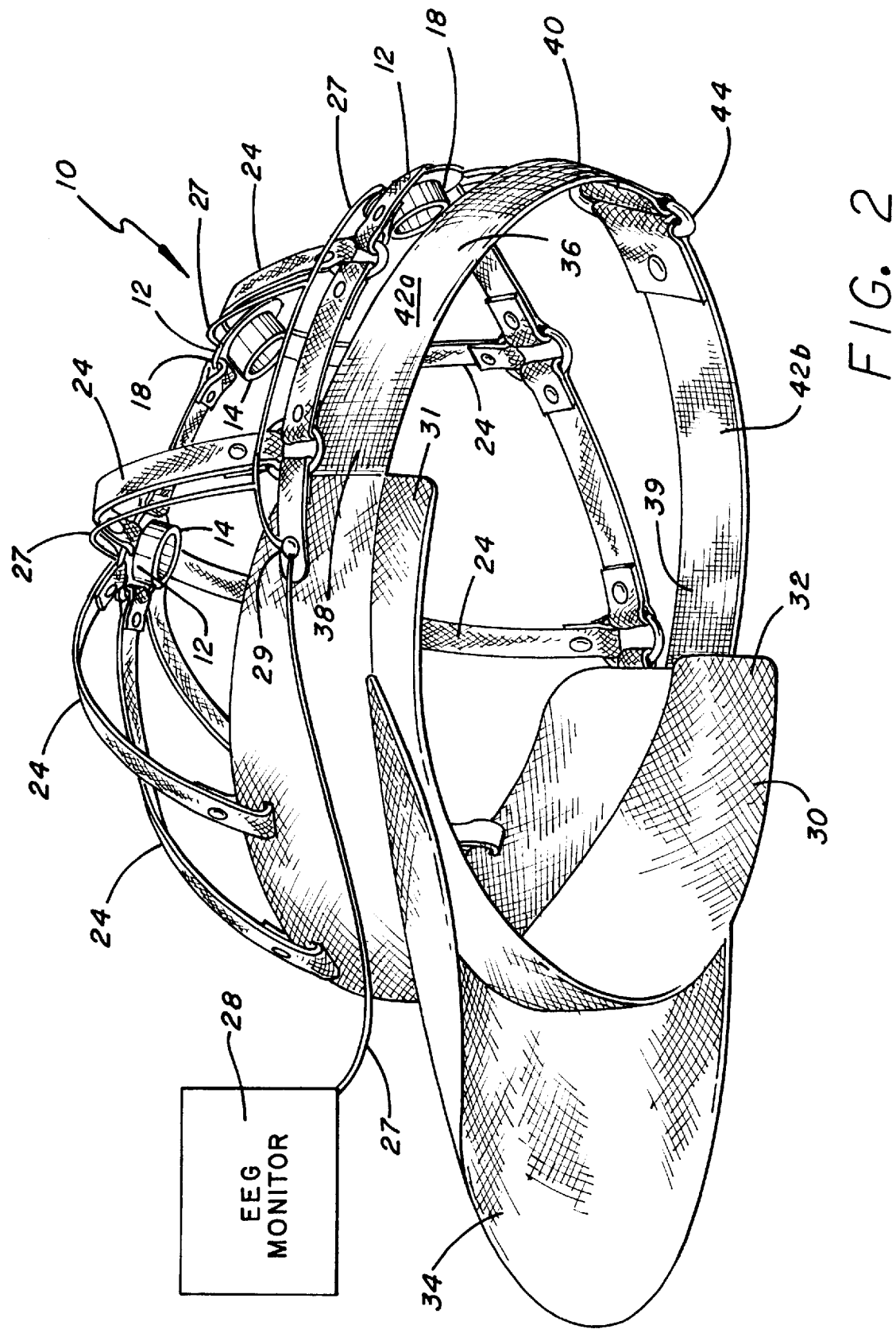
FIG. 2 is a bottom perspective view of the EEG electrode locator headgear of FIG. 1.

In a presently preferred embodiment, as is best seen in FIGS. 1 and 2, the EEG electrode locator headgear advantageously includes a front pad of material 30, having a first end 31 and a second end 32. The front pad of material is adapted to extend across a user's forehead to provide a secure footing for the EEG electrode locator headgear. The front pad of material is preferably made of a non-elastic electrically conductive fabric material, such as fabric containing silver or other metallic, electrically conductive threads, for example. A front visor or bill 34 is preferably attached to the front pad of material. A base strap assembly 36 is also provided, having a first anterior end 38 connected to the first end of the front pad of material, and a second anterior end being connected at the first anterior end 38, and the second elastic edge strap 42b being connected at the second anterior end 39 of the front pad of material, and adjustably connected together at the posterior end 40. The plurality of locator straps preferably form a network of locator straps connected to the front pad of material, the base strap assembly, and to the plurality of EEG electrode locators for accurately positioning the plurality of EEG electrode locators positioned relative to the scalp of a user. The plurality of locator straps are preferably made of elastic material, such that the locator straps bias the plurality of electrode locators with a biasing pressure toward the user's scalp, and thereby bias the electrodes inserted into the electrode locators toward the user's scalp, to provide a stable electrode-scalp interface capable of producing a high signal quality.

Figure 8:
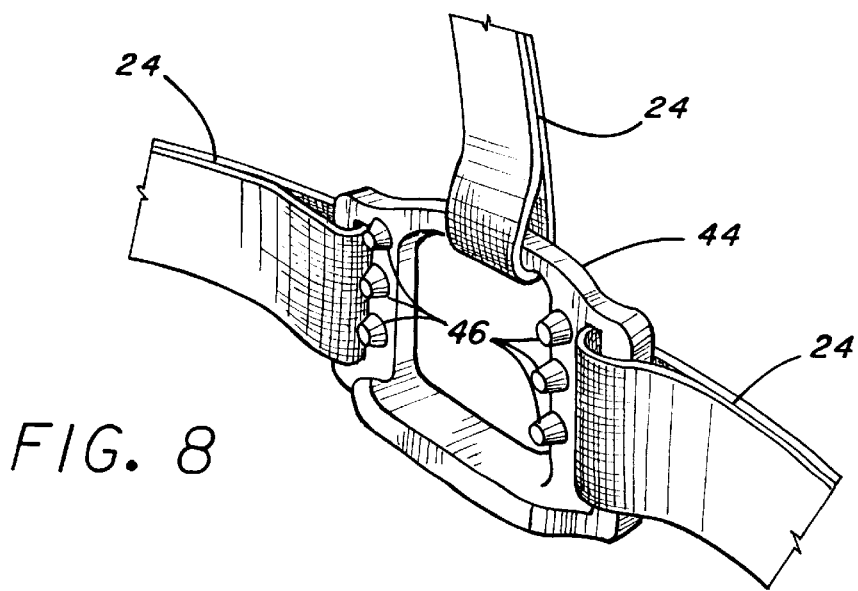
FIG. 8 is a perspective view of an occipital locator of the base strap of the EEG electrode locator headgear of FIG. 1.

In another presently preferred embodiment illustrated in FIG. 8, the base strap assembly includes an occipital locator device 44 adapted to be seated on a region of the user's scalp over the user's occipital bone. The base strap assembly first and second elastic edge straps are thus preferably connected at one end to the front pad of material, and adjustably connected at the other end to the occipital locator device, which is currently preferably a ring, such as a D ring, for example, having a plurality of feet 46 adapted to be positioned over the user's occipital bone.

In another preferred aspect of the EEG electrode locator headgear, an anterior locator strap 50 is connected to the front pad of material, with a free end 52 adapted to be positioned over the user's nasium to confirm accurate placement of the electrode locators.

Figure 3:
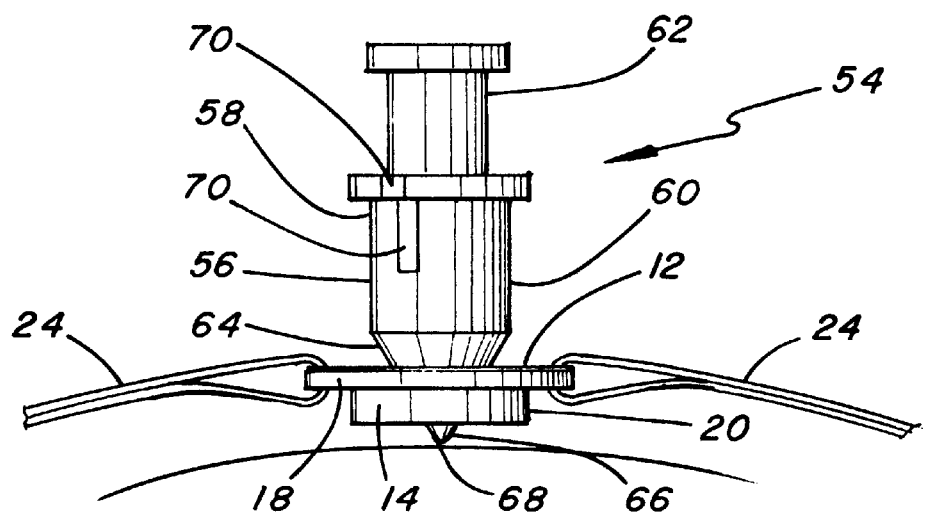
FIG. 3 is a side elevational view of an EEG electrode locator of the EEG electrode locator headgear of FIG. 1, illustrating an EEG electrode, plunger assembly being inserted in the EEG electrode locator.

The EEG electrodes are preferably of the type that are disposable, and as is illustrated in FIGS. 3, 4 and 6, are adapted to be seated in the plurality of electrode locators, respectively. In a presently preferred embodiment, a plunger assembly 54 is also provided that is adapted be used for preparation of the scalp of the user for placement of the disposable electrodes, and is adapted to cooperate with the plurality of electrode locators. In one presently preferred embodiment, the plunger assembly includes a hollow tubular base 56 having an upper portion 58 and a lower portion 60, and a plunger 62 adapted to be received in the hollow tubular base. The upper portion of the plunger assembly tubular base preferably can be seated in the electrode locators by interference or snap fit, although a slot and groove interlocking assembly may alternatively be provided for seating the plunger assembly tubular base in the electrode locators. The lower portion of the hollow tubular base advantageously includes a plurality of flexible, resilient fingers 64 having distal ends 66 biased to come together at a common distal central location 68, and that can be spread by the plunger 62 in order to part the hair of the scalp of the user. As can be seen in FIG. 4, the plunger and electrode may also be used for spreading the flexible, resilient fingers of the tubular base of the plunger assembly. In a presently preferred aspect, the spreadable fingers are formed of a plastic, such as a thermoplastic that can be readily molded, for example. The plunger assembly hollow tubular base preferably includes an electrical conductor such as the electrical conductor strip 26 adapted to be electrically connected between an electrode inserted in the hollow tubular base and a corresponding electrical conductor of one of the electrode locators for conducting EEG signals from the electrodes to the EEG monitor 28. The distal flexible, resilient fingers of the plunger hollow tubular base can be spread by insertion of an electrode through the plunger hollow tubular base, so that the plunger assembly can be used to simultaneously part the hair by spreading of the distal fingers of the plunger hollow tubular base, seat the disposable electrode, and optionally also abrade the scalp of the user at the intended location of the electrode, such as by manually twisting the hollow tubular base to rub the distal ends of the distal fingers against the scalp of the user.

Figure 5A:
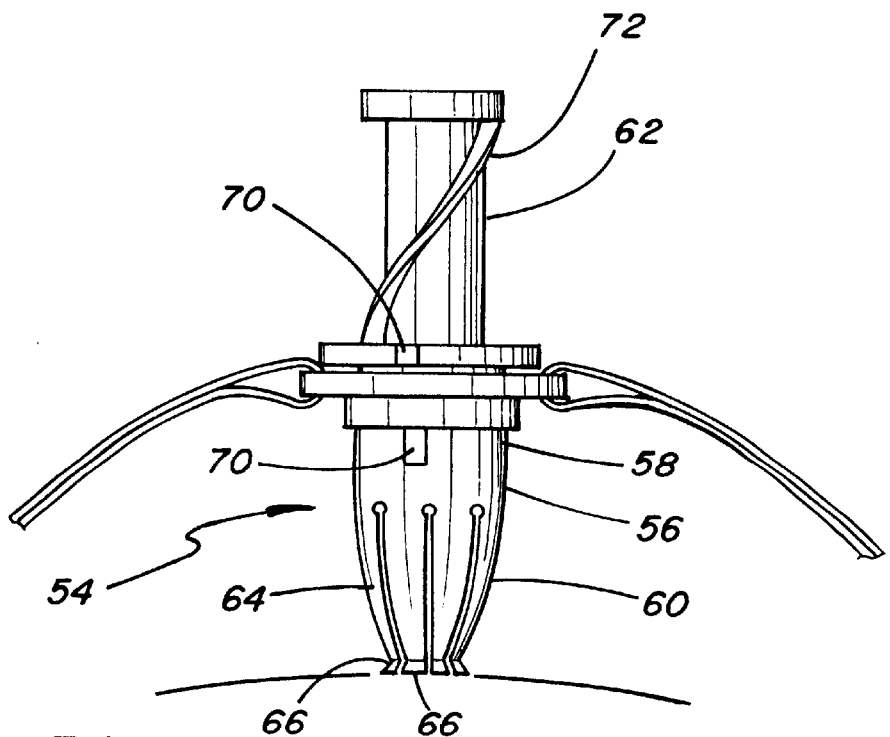
FIG. 5A is a side elevational view of an EEG electrode locator of the EEG electrode locator headgear of FIG. 1, illustrating an alternate plunger assembly being inserted in the EEG electrode locator.
Figure 5B:
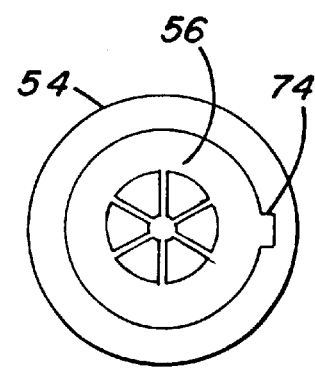
FIG. 5B is a top plan view of the plunger assembly of FIG. 5A.

In another presently preferred alternate embodiment illustrated in FIGS. 5 and 6, the plunger can be provided with an external helical rib 72, and the hollow tubular base can be provided with a corresponding internal groove 74 for receiving and guiding the external helical rib of the plunger as the plunger and electrode are inserted in the hollow tubular base of the plunger assembly, to provide a predetermined turning and torque to the plunger as it is inserted.

Figure 11:
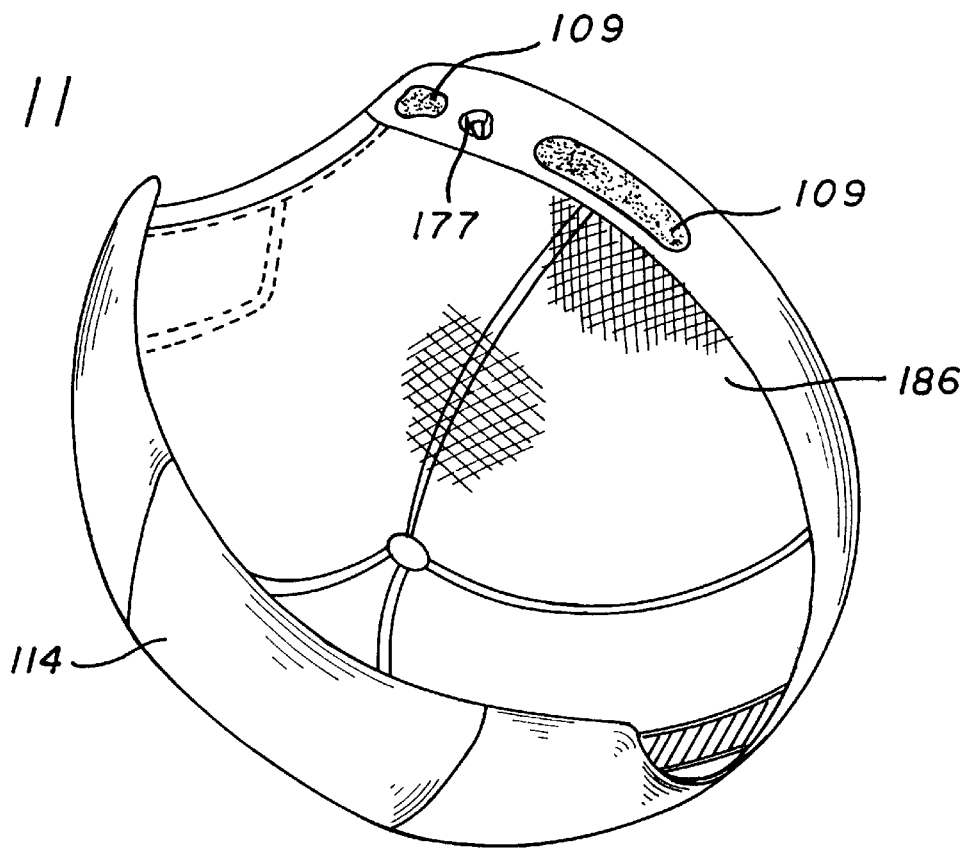
FIG. 11 is a bottom perspective view of the outer cap shell of the EEG electrode locator headgear of FIG. 9.
Figure 9:
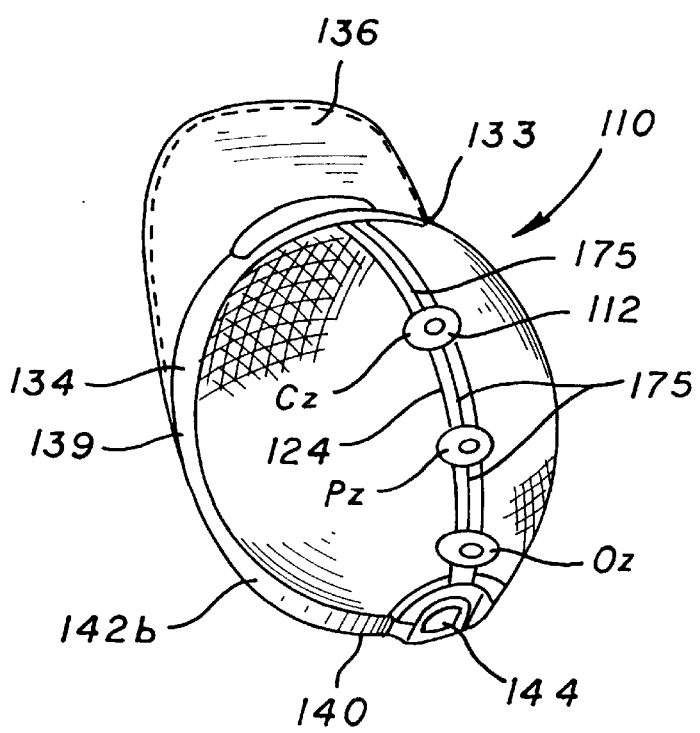
FIG. 9 is a top perspective view of a second preferred embodiment of the EEG electrode locator headgear, without the cap shell to show the positions of the electrode locations.
Figure 12:
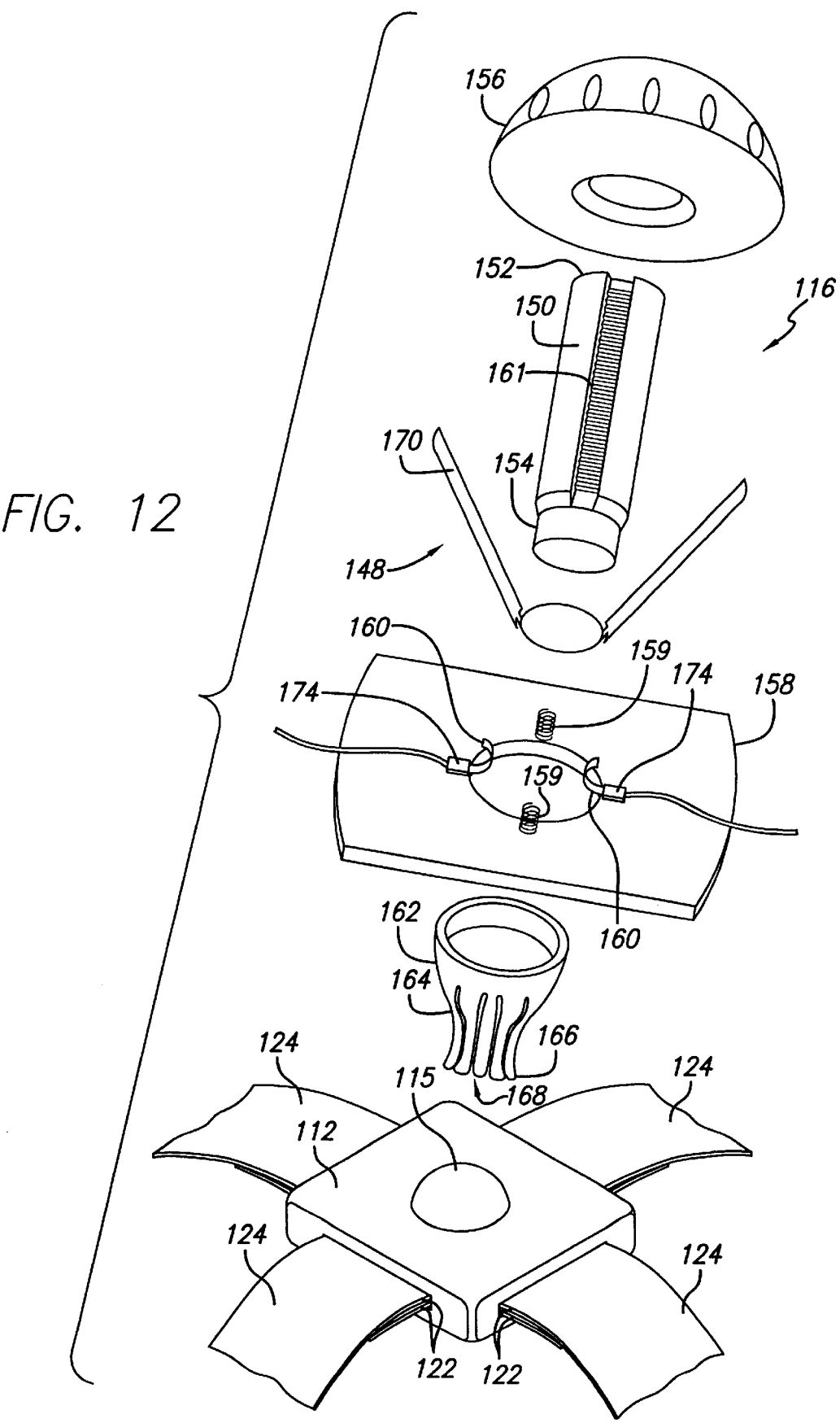
FIG. 12 is an exploded view of an EEG electrode plunger assembly of the embodiment of FIG. 9.

Referring to FIGS. 9 to 17, in another presently preferred embodiment, the invention provides for an EEG electrode locator headgear 110 having a cap portion 111 with a plurality of EEG electrode locators 112 for receiving EEG electrodes for accurate positioning on the scalp of a user. An outer cap shell 114 that can be made of cotton, wool or other fabric, for example, or the like, may be fitted over and connectable to the cap portion by one or more fasteners such as an electrically conductive connector 113, or other similar fasteners such as snaps, hook and loop fasteners 109, buttons, or the like, to protect and conceal the EEG electrode locators. The outer cap shell may also include electromagnetic shielding, as will be described further below, which is to be electrically connected through the electrically conductive connector to the front pad of material that also serves as an electrical ground. The electrode locators each have a tubular opening 115 adapted to receive an EEG electrode 116, as is illustrated in FIGS. 12, 16 and 17. As is shown in FIG. 12, the EEG electrode locators each include a plurality of slots 122 for receiving locator straps 124 that are currently preferably formed of elasticized fabric, in order to assist in biasing the electrode locators toward the scalp of the user, but non-elastic straps, such as fabric or nylon, for example, may also be suitable. Although a single locator strap is illustrated in FIG. 9 for locating each of the EEG electrode locators, additional locator straps may also be attached to the EEG electrode locators as is illustrated in FIG. 12.

In this embodiment, the EEG electrodes are preferably adapted to be connected for electrical communication by radio frequency (RF) transmission with an EEG monitor, which is preferably a portable EEG monitor for ambulatory use, as will be further explained below. Three EEG electrode locators are preferably provided that are adapted to be positioned at the top central (Cz), parietal (Pz), and occipital (Oz) positions relative to the scalp of a user, although alternatively additional or fewer electrode locators may also be provided in the headgear for locating EEG electrodes according to the International 10/20 system.

Figure 10:
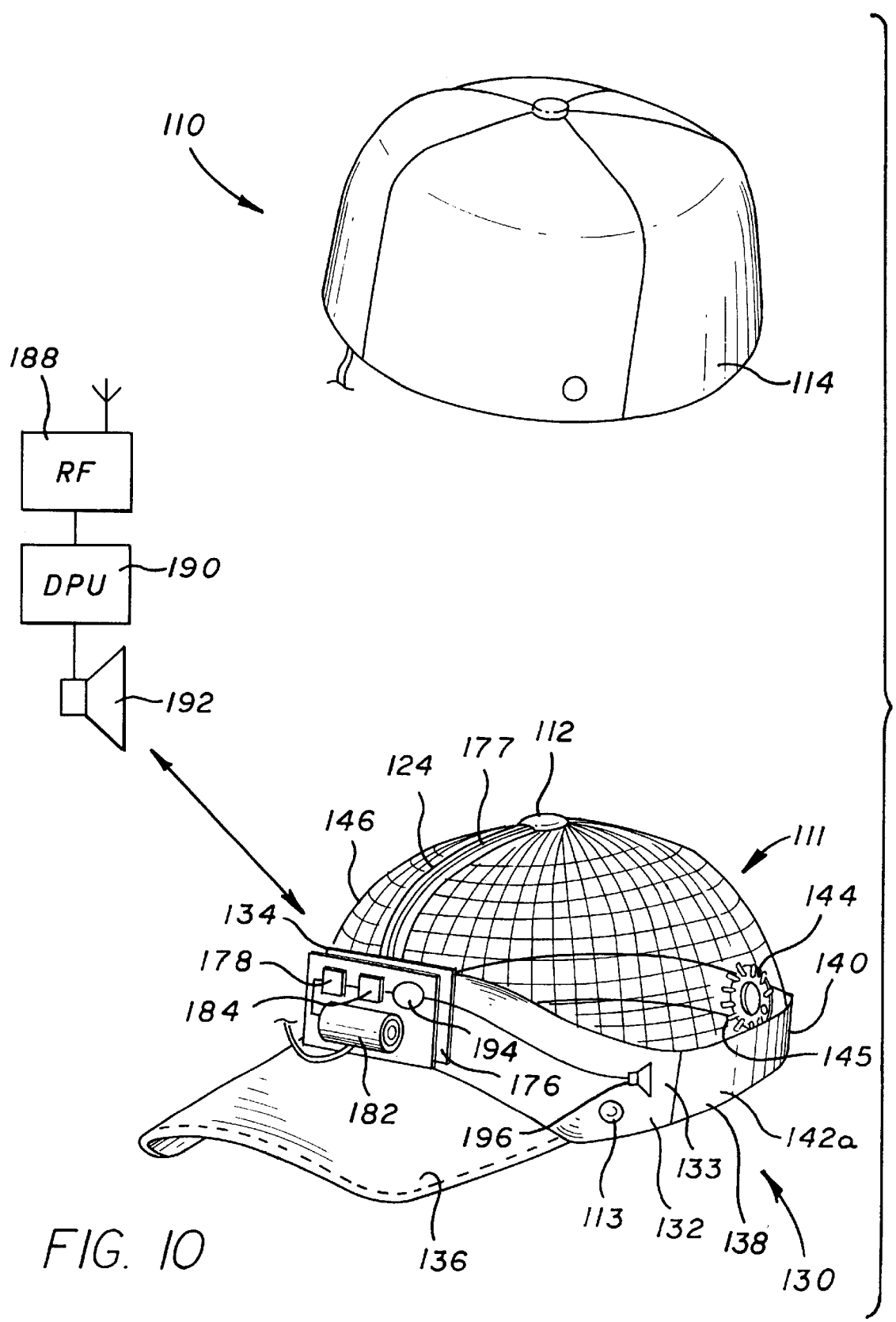
FIG. 10 is an exploded perspective view of the second preferred embodiment of the EEG electrode locator headgear of the present invention.

Referring to FIGS. 9 to 12, the base strap assembly 130 of the EEG electrode locator headgear includes a front pad of material 132, having first and second ends 133, 134, adapted to extend across a user's forehead to provide a secure footing and electrical ground for the EEG electrode locator headgear on the user's forehead. The front pad of material is preferably made of a non-elastic electrically conductive fabric material, as described above. A front visor or bill 136 is preferably attached to the front pad of material. The base strap assembly has a first anterior end 138 connected to the first end of the front pad of material, and a second anterior end 139 connected to the second end of the front pad of material, and a posterior end 140. Together, the front pad of material and the base strap assembly are adapted to be secured comfortably around the circumference of the user's head, and the base strap assembly is adjustable. The base strap preferably comprises a pair of adjustable elastic edge straps, with the first elastic edge strap 142a connected at the first anterior end 138, and the second elastic edge strap 142b being connected at the second anterior end 139 of the front pad of material, and adjustably connected together at the posterior end 140. As is illustrated in FIGS. 9 and 10, the base strap assembly includes an occipital locator device 144 adapted to be seated on a region of the user's scalp over the user's occipital bone. The base strap assembly first and second elastic edge straps are thus preferably connected at one end to the front pad of material, and adjustably connected at the other end to the occipital locator device, which in another currently preferred embodiment comprises an annular ring having a plurality of feet 145 adapted to be positioned around and over the user's occipital bone.

As is illustrated in FIGS. 9 to 11, a stretch mesh cap 146 of elastic, fabric material may also be provided in addition to, or as an alternative to, the locator straps, connected to the front pad of material, the base strap assembly, and to the plurality of EEG electrode locators for accurately positioning the plurality of EEG electrode locators relative to the scalp of a user. The stretch mesh and locator straps are preferably made of elastic material, in order to bias the electrode locators and electrodes with a downward biasing pressure toward the user's scalp, to provide a stable electrode-scalp interface capable of producing a high signal quality.

Referring to FIGS. 12 to 17, the EEG electrodes are preferably of the type that are disposable, and are adapted to be seated in the electrode locators. In this embodiment, each of the EEG electrodes include a plunger assembly 148 with a generally cylindrical plunger member 150 having an upper portion 152 and a lower portion 154. The plunger assembly may also include a cap 156 connected to the upper portion of the plunger member. As is illustrated in FIG. 12, the plunger assembly is adapted to be received in a circuit board base member 158 mounted on or in an electrode locator and having a plurality of spring loaded detents 159 and electrically conductive spring connectors 160. The cylindrical plunger member preferably has a plurality of grooves or ratchet strips 161 for engagement with the corresponding spring loaded detents in the circuit board member for seating the plunger assembly tubular base in the electrode locators.

The lower portion of the plunger preferably includes an electrically conductive spreader member 162 having a plurality of flexible, resilient fingers 164 having distal ends 166 biased to come together at a common distal central location 168, and that can be spread by the application of downward force of the plunger assembly against a user's scalp in order to part the hair of the scalp of the user. The spreader member also includes an electrically conductive thick cushion portion 169 that will rest against the scalp of the user after the electrode has been pressed downward to seat the electrode on the user's scalp and spread the flexible, resilient fingers, to cushion the pressure of the electrode on the user's scalp for additional comfort. As is illustrated in FIG. 12, an electrical conductor strip 170 is disposed over the lower portion and opposing sides of the cylindrical plunger member, to provide electrical communication between the electrical spring connectors of the electrode locator circuit board and the electrically conductive spreader member for communicating EEG signals from the electrodes to the EEG monitor. The initial positioning of the flexible, resilient fingers prior to spreading of the fingers can provide a seal and protection of a conductive gel 172 that can also be placed adjacent to the cushion portion of the spreader member and between the flexible, resilient fingers for additional comfort of the user and improved acquisition of EEG signals from the user's scalp.

The distal flexible, resilient fingers of the plunger hollow tubular base can be spread by insertion of an electrode through an electrode locator to press downwardly against the user's scalp 171, so that the plunger assembly can be used to simultaneously part the hair by spreading of the distal fingers of the plunger hollow tubular base and seat the disposable electrode. The distal fingers can also be used to abrade the scalp of the user at the intended location of the electrode, such as by manually twisting the hollow tubular base to rub the distal ends of the distal fingers against the scalp of the user. The spreader member and the spreadable fingers are currently preferably formed of an electrically conductive silicone, such as silicone containing carbon, or containing other similar electrically conductive material, for example, for improved acquisition of EEG signals from the user's scalp.

Referring to FIG. 12, in a currently preferred embodiment, operational pre-amplifiers will be provided at each electrode site, so that it will not be necessary to provide a second stage differential amplification of the acquired EEG signals. In one presently preferred implementation, each pre-amplifier 174 will be mounted on the electrode locator, such as on the circuit board base member 173 mounted on the upper surface of the electrode locator, for example. Alternatively, the circuit board base member and pre-amplifier may be contained within a housing provided by the electrode locator, or the pre-amplifier may be provided in the electrodes. Referring to FIGS. 9 and 10, the EEG signals from the Cz, Pz, and Oz electrode locators will be routed by wires 175 from the pre-amplifiers via electrical connector 177, which connects with electrical connector 113, as the differential inputs of a Sigma Delta analog to digital converter 176 currently preferably mounted on a circuit board at the front of the headgear, and an input is provided to the pre-amplifiers from the front ground pad sewn into the portion of the headgear that contacts the forehead. The output of the analog to digital converter will result in a differential recording of EEG signals. The gain from the Cz electrode locator is preferably set to a gain of one, while the gains for the Pz and Oz electrode locators will be greater, and are typically 10. All filtering of the EEG signals will typically be performed digitally by programming of the analog to digital converter. The analog to digital converter, microprocessor 178, batteries 182, and an RF transmitter 184 are preferably mounted at the front of the headgear. A Faraday shield 186 is also preferably incorporated into the headgear, such as electromagnetic shielding material sewn into the outer cap shell, for example, as shown in FIG. 11, to create a Faraday shield to shield the pre-amplifiers from external noise and artifacts which may result from the use of the RF transmitter. Radio frequency transmission is currently preferred for communication of the EEG signals to an RF receiver 188 connected to a computing device 190 used for acquiring and analyzing the digital EEG signals from the user, so that no wires are required to connect the user to a recording and/or data analysis device. In one presently preferred configuration, the computing device is a data processing unit (DPU) used to acquire and analyze EEG signals from the user, and to provide feedback to the user.

The DPU preferably includes a digital signal processing (DSP) chip, power supply, digital to analog converter, a speaker 192, and batteries (not shown), so that the DPU is completely portable. The DPU can thus acquire EEG signals from the EEG electrode locator headgear, run the EEG data analysis algorithms, and use the digital to analog converter and speaker to generate audio feedback alert messages to the user. In order to provide the audio messages to the user that may be required in noisy environmental conditions, the RF transmitter 184 of the EEG electrode locator headgear and the RF receiver 188 connected to the DPU are preferably bidirectional RF transmitter-receivers, and an amplifier 194 and speaker 196 are also mounted on the EEG electrode locator headgear. Thus, when the DPU determines that an audio alert message or verbal message should be transmitted to the user, a signal is transmitted from the DPU to the EEG electrode locator headgear to present a specific message. Audio messages can be stored in analog format in flash memory in the EEG electrode locator headgear where the analog to digital converter, power supply and processor are mounted. The analog message can then be presented to the user either through one or more speakers mounted on the EEG electrode locator headgear, or through an earphone that attaches to a connector incorporated into the EEG electrode locator headgear.

Figure 18:
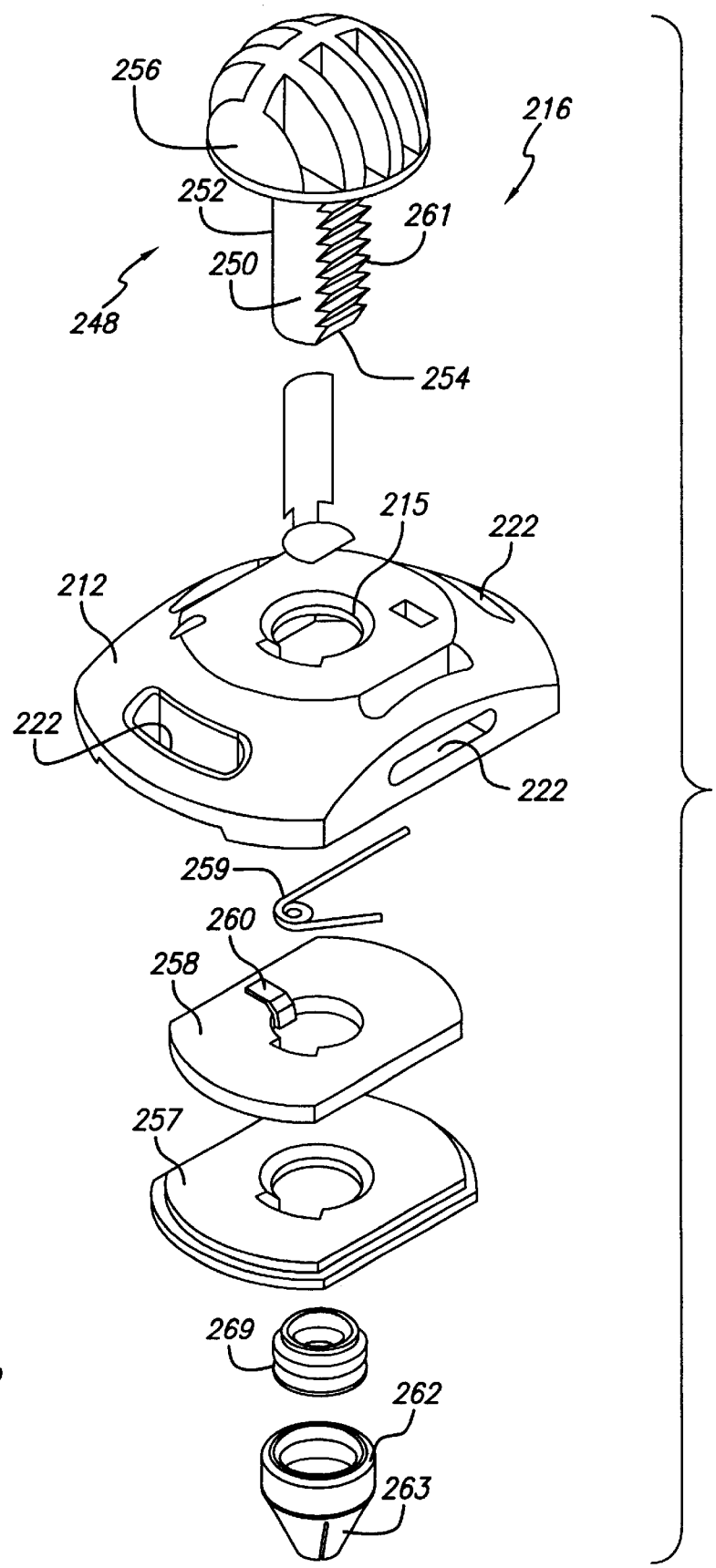
FIG. 18 is an exploded view of an alternate embodiment of an EEG electrode plunger assembly according to the present invention.
Figure 19:
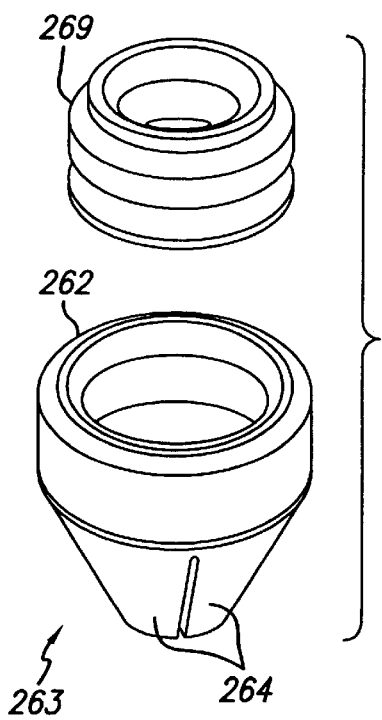
FIG. 19 is an exploded perspective view of one presently preferred embodiment of an electrically conductive spreader member of the EEG electrode plunger assembly of FIG. 18.
Figure 20:
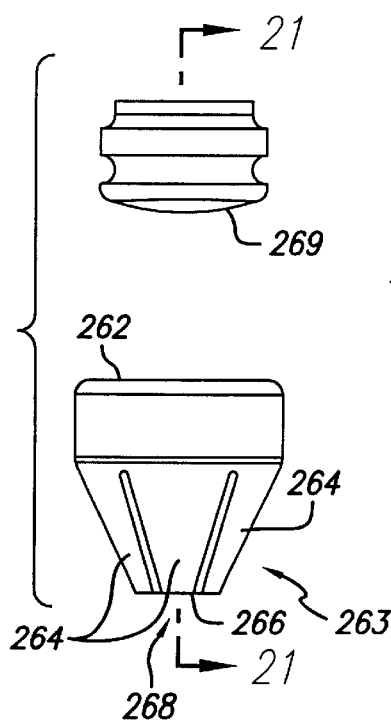
FIG. 20 is an exploded side elevational view of the electrically conductive spreader member of the EEG electrode plunger assembly of FIG. 19.
Figure 21:
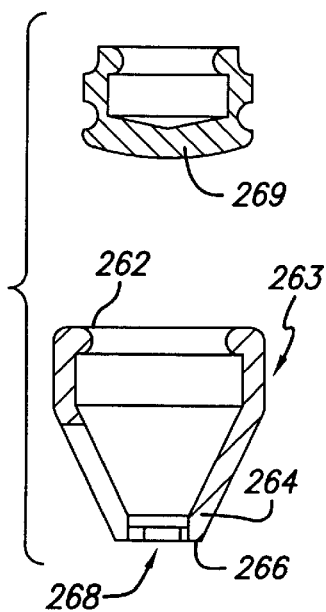
FIG. 21 is a sectional view of the electrically conductive spreader member of FIG. 20 taken along line 21—21.
Figure 22:
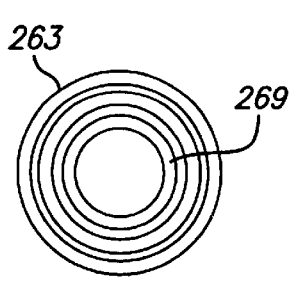
FIG. 22 is a top plan view of the electrically conductive spreader member of the EEG electrode plunger assembly of FIG. 19.
Figure 23:
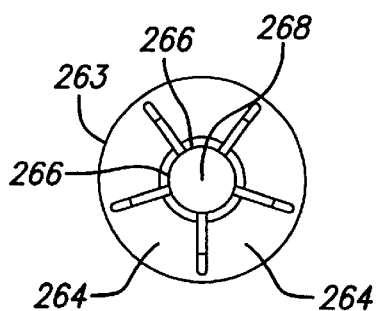
FIG. 23 is a bottom plan view of he electrically conductive spreader member of the EEG electrode plunger assembly of FIG. 19.

Referring to FIG. 18, illustrating an assembly of an alternate embodiment of an electrode locator and an electrode according to the invention, it can be seen that the electrode locator assembly 212 provides a tubular opening 215 for receiving an EEG electrode 216. The EEG electrode locators each include a plurality of slots 222 for receiving locator straps, as described above. The EEG electrodes include a plunger assembly 248 with a generally cylindrical plunger member 250 having an upper portion 252 and a lower portion 254. The plunger assembly may also include a cap 256 connected to the upper portion of the plunger member. The plunger assembly is adapted to be received in a circuit board base member 258 mounted in the electrode locator with a spring detent 259 and one or more electrically conductive connectors 260. The circuit board base member can be retained in the electrode locator assembly by a retainer member 257 fitting in the bottom of the electrode locator, for example. The cylindrical plunger member preferably has a plurality of grooves in a side ratchet strip 261 for engagement with the corresponding spring detent in the circuit board member for seating the plunger assembly tubular base in the electrode locators.

Referring to FIGS. 18–23, the lower portion of the plunger preferably includes an electrically conductive spreader member 262 having a spreadable base portion 263 comprising in this embodiment a plurality of flexible, resilient fingers 264 having distal ends 266 biased to close together approximately at a common distal central location 268, and that can be spread by the application of downward force of the plunger assembly against a user's scalp in order to part the hair of the scalp of the user. The spreader member also includes an electrically conductive intermediate portion with a thick electrically conductive cushion portion 269 that will rest against the scalp of the user after the electrode has been pressed downward to seat the electrode on the user's scalp and spread the flexible, resilient fingers, to cushion the pressure of the electrode on the user's scalp for additional comfort. Alternatively, an electrically conductive gel cap may also be provided within the spreader member base portion to be pressed against the scalp by the electrically conductive intermediate cushion portion. An electrical conductor strip 270 is disposed over the lower portion and opposing sides of the cylindrical plunger member, to provide electrical communication between the one or more electrical connectors of the electrode locator circuit board and the electrically conductive spreader member for communicating EEG signals from the electrodes to the EEG monitor. The initial positioning of the flexible, resilient fingers prior to spreading of the fingers can provide a seal and protection of the conductive gel cap, when used.

The distal flexible, resilient fingers of the plunger hollow tubular base can be spread by insertion of an electrode through an electrode locator to press downwardly against the user's scalp, so that the plunger assembly can be used to simultaneously part the hair by spreading of the distal fingers of the plunger hollow tubular base and seat the disposable electrode. As described above, the distal fingers can also be used to abrade the scalp of the user at the intended location of the electrode, such as by manually twisting the hollow tubular base to rub the distal ends of the distal fingers against the scalp of the user. The spreader member, intermediate cushion portion, and spreadable fingers are currently preferably formed of an electrically conductive silicone, such as silicone containing carbon, or containing other similar electrically conductive material, for example, for improved acquisition of EEG signals from the user's scalp. Operational pre-amplifiers will preferably be provided at each electrode site, so that it will not be necessary to provide a second stage differential amplification of the acquired EEG signals, as described above.

Referring to FIGS. 24–31, in another presently preferred embodiment, the electrode assembly has an electrically conductive spreader member 262' having a spreadable base portion 263' comprising a flexible and resilient, tapered base member 264' having a generally annular but uneven lower end surface 265', with slightly raised shoulder portions 266' and lower extending flange portions 267'. The flexible, resilient tapered base member can be spread by the application of downward force of the plunger assembly against a user's scalp in order to part the hair of the scalp of the user. The spreader member also includes an electrically conductive intermediate portion with a thick cushion portion 269' that will rest against the scalp of the user after the electrode has been pressed downward to seat the electrode on the user's scalp and spread the flexible, resilient fingers, to cushion the pressure of the electrode on the user's scalp for additional comfort. Alternatively, an electrically conductive gel cap may also be provided within the spreader member base portion to be pressed against the scalp by the intermediate cushion portion, and the tapered base member can provide a seal and protection of the conductive gel cap, when used.

As described above, the distal spreader member of the plunger hollow tubular base can be spread by insertion of an electrode through an electrode locator to press downwardly against the user's scalp, so that the plunger assembly can be used to simultaneously part the hair by spreading of the tapered base member of the spreader. The uneven bottom surface of the tapered base member can also be used to abrade the scalp of the user at the intended electrode site, such as by manually twisting the hollow tubular base to rub the distal ends of the distal fingers against the scalp of the user. The spreader member, intermediate cushion portion, and spreadable fingers are currently preferably formed of an electrically conductive silicone, such as silicone containing carbon, or containing other similar electrically conductive material.

It is contemplated that the EEG electrode locator headgear of the invention can be utilized in three principal modes in a portable EEG monitoring system for ambulatory use. All three modes share the same basic features, including high input impedance low noise pre-amplifiers mounted at the electrode site. The three modes would also preferably utilized a Sigma-delta Analog/Digital (A/D) converter which is programmed to provide sampling rates, and filtering requirements specified by the EEG monitoring software (i.e., 256 samples/sec, high and low pass filter cutoffs). Other types of A/D converters can be used (e.g., successive approximation), however, based on present technology circuitry must be added with increase the weight, size and power consumption of the system to provide the appropriate analog and/or digital filtering. A micro-controller would also be provided that can be programmed to operate the A/D, control the optional impedance monitoring circuitry, select/transmit messages to be transmitted by the voice unit to the speaker, and operate the radio transceiver, when applicable. In addition, voice unit circuitry will generate pre-recorded analog auditory alarms or verbal messages transmitted to a speaker to notify the user based on the requirements of the B-Alert software.

The impedance monitoring circuitry and A/D chip will typically be mounted on an analog board, and the micro-controller, power supply elements, battery, voice unit circuitry and radio transceiver will typically be mounted on a second digital board to minimize the noise contributed by the system to the analog inputs. In one presently preferred implementation, all components can be mounted on a single board, with an electro-mechanical layout that isolates the radio transceiver and power supply to minimize system noise.

The EEG monitoring system software can also provide for monitoring noise attributed to excessive scalp-electrode impedance without the use of impedance monitoring circuitry by calculating the magnitude of 60 Hz interference. Alternatively, impedance circuitry can be implemented which produces a low level driving signal across the electrodes and then measures the induced voltage or current depending on the circuit. This approach can be operated in time sharing mode while acquiring the EEG signals, or continuous monitoring is possible if the frequency of the impedance signal generator is outside the frequency range used for the EEG monitoring system software (i.e., 0.5 to 128 Hz).

A voice unit for playing audio messages can utilize analog memory devices (such as ISD33120) or a D/A converter and standard digital memory. To provide sufficient volume to the speaker, an audio power amplifier may be required.

Figure 29:
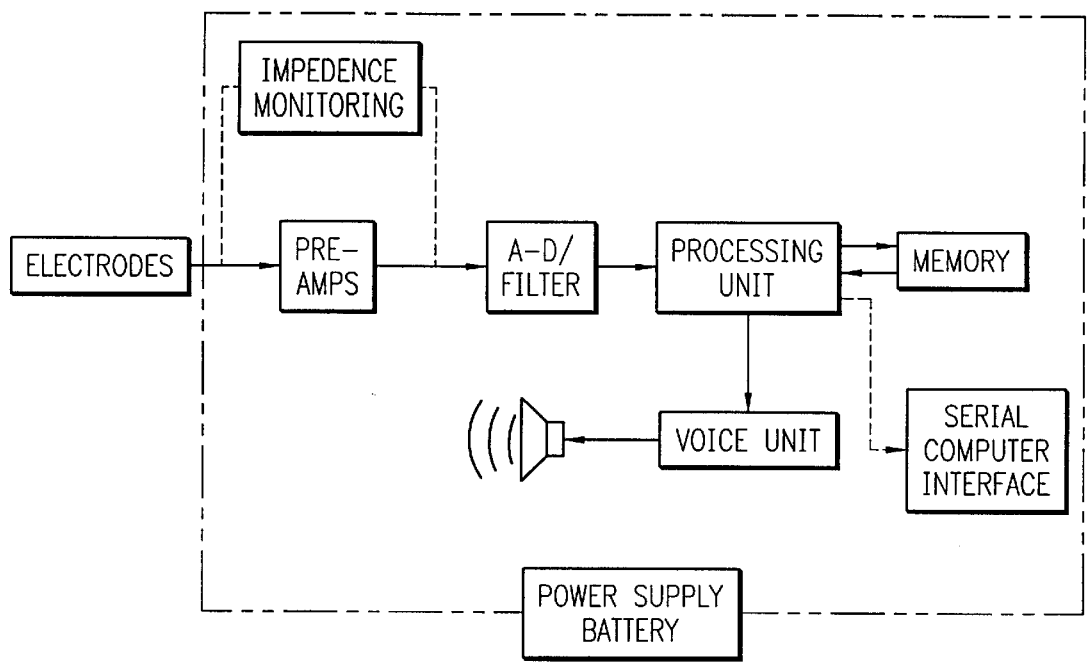
FIG. 29 is a schematic diagram of a self-contained processing mode of utilizing the EEG electrode locator headgear of the invention in an EEG monitoring system.

Referring to FIG. 29, when the processing unit in the self-contained processing mode is a micro-controller, the system can operate the portion of the EEG monitoring system software designed to acquire high quality EEG recordings by monitoring and providing feedback for excessive movement and muscle artifacts. If the processing unit utilizes a Digital Signal Processing (DSP) chip, this mode is capable of processing the EEG monitoring system alertness monitoring software in real-time. Flash memory can be used to store the EEG monitoring system software and the digital data acquired while the system is in use. A serial computer interface circuitry will allow software to be loaded in the flash memory for use by the DSP and to download data stored in flash memory to computer for off-line analysis and storage. The self-contained processing mode with the DSP chip will be a preferred embodiment for ambulatory use of the system at such time as battery storage technologies improve the capacity of small disposable batteries, or the power required to operate a DSP chip and the EEG monitoring system software becomes less than that required to operate the radio transceiver.

Figure 30:
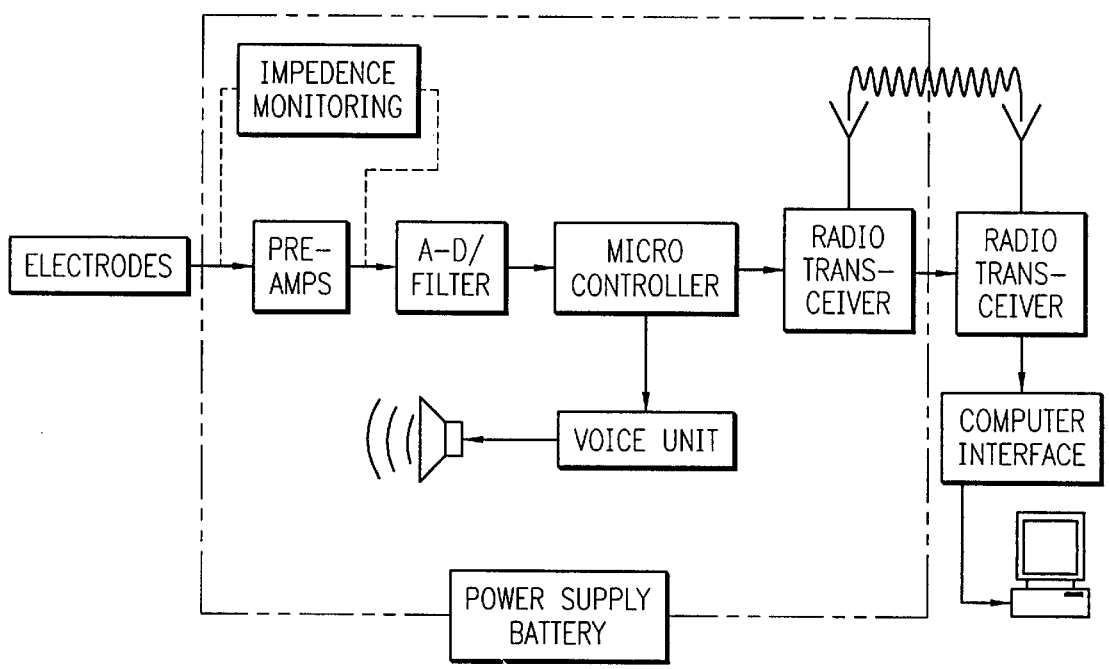
FIG. 30 is a schematic diagram of a computer interfaced processing mode of utilizing the EEG electrode locator headgear of the invention in an EEG monitoring system.

Referring to FIG. 30, the computer interfaced processing mode is designed for use of the electrode locator headgear in conjunction with a laptop or workstation computer (PC). A radio transceiver is integrated with the PC through a computer interface. The mode is capable of running the EEG monitoring system software in the data acquisition mode, or if the CPU of the PC is sufficiently fast, running the EEG monitoring system software for real-time processing. The radio transceiver interfaced with the PC (RTC) can transmit control messages initiated by the EEG monitoring system software to the radio transceiver located on the electrode locator headgear. The micro-controller on the electrode locator headgear will interpret and implement the control messages, including impedance monitoring and deliver of audio or verbal messages to the user.

Figure 31A:
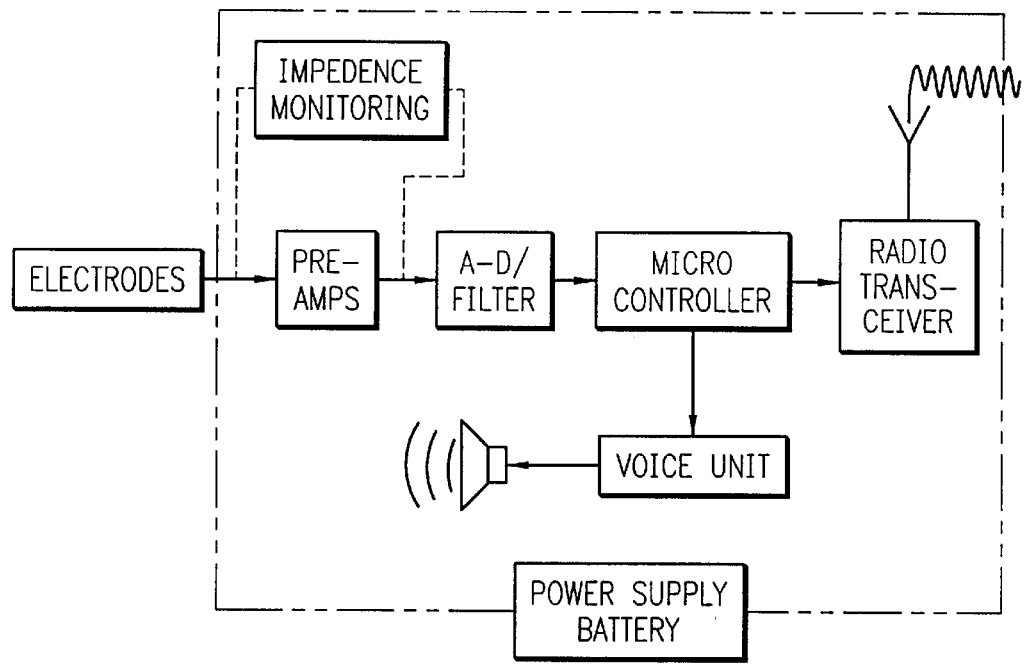
FIGS. 31A and 31B illustrate a schematic diagram of a modular real-time processing mode of utilizing the EEG electrode locator headgear of the invention in an EEG monitoring system.
Figure 31B:
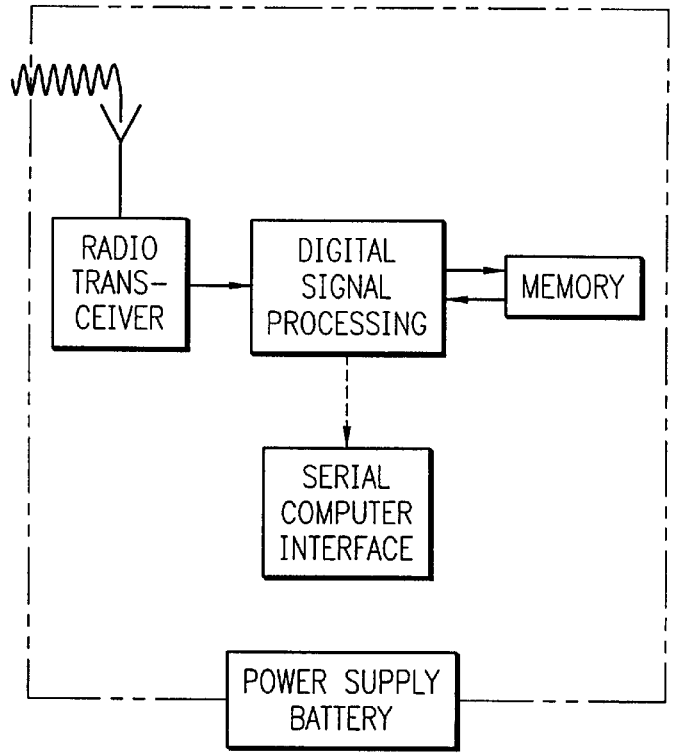

Referring to FIGS. 31A and 31B, the modular real-time processing mode provides all components necessary to operate the EEG alertness monitoring software in real-time packaged in a device the size of a pager. Digitized data transmitted from the electrode locator headgear will be received by RTC, processed using the EEG monitoring system software and DSP chip. Control messages initiated by the EEG monitoring system software will be transmitted by the RTC to the electrode locator headgear, which will then be interpreted and implemented by the circuitry located on the electrode locator headgear. Data will be stored on the flash memory for use by the EEG monitoring system software and can be downloaded to a PC using the serial computer interface.

It should be understood that the individual EEG electrodes can alternatively be individually or collectively directly connected such as by one or more cables to an EEG signal monitor, and that other conventional modifications may also be suitable. Although the EEG electrode locator headgear of the invention is advantageously adapted to be usable without a chin strap by an adult user, it should be appreciated that the EEG electrode locator headgear of the invention could also be adapted to include a chin strap for use by children or to meet the special requirements of an individual user. In addition, although the present invention contemplates the location of disposable EEG electrodes in individual EEG electrode locators, it should be appreciated that combined EEG electrode and locator assemblies, such as active, amplified electrodes, for example, may be incorporated into the headgear of the locations of the EEG electrode locators, in the same or a similar manner. Alternatively, active electrodes or preamplifiers could be incorporated into the plunger or connected to the electrical conductor of the electrode locator. It will thus be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An electroencephalograph (EEG) electrode locator headgear, comprising:
   a base strap assembly adapted to be secured comfortably around the circumference of a user's head;

an elastic, stretchable cap portion connected to said base strap assembly;

a plurality of EEG electrode locators mounted to said elastic, stretchable cap portion for accurately positioning said plurality of EEG electrode locators relative to the user's scalp, and for biasing said plurality of electrode locators toward the user's scalp; and a plurality of EEG electrodes adapted to be received in and cooperate with said plurality of EEG electrode locators, respectively, each of said EEG electrodes including a plunger assembly adapted to prepare the user's scalp and to seat the electrode in one of said EEG electrode locators, said plunger assembly including a plunger member having upper and lower portions, and said plunger assembly including an electrically conductive spreader member mounted to said lower portion of said plunger member, said spreader member having a plurality of flexible, resilient fingers having distal ends biased to meet at a common distal central location, and said flexible, resilient fingers being adapted to spread apart by exertion of downward pressure of said plunger assembly against the user's scalp and to thereby part the hair of the user's scalp.

2. The EEG electrode locator headgear of claim 1, wherein said plunger assembly is adapted to be inserted in the electrode locator to spread the distal flexible, resilient fingers.

3. The EEG electrode locator headgear of claim 1, wherein said plunger assembly comprises a cap connected to the upper portion of the plunger member.

4. The EEG electrode locator headgear of claim 1, wherein said spreader member comprises a cushion portion located between said flexible, resilient fingers adapted to rest against the user's scalp after the electrode has been pressed downward to seat the electrode on the user's scalp and spread the flexible, resilient fingers, to cushion the pressure of the electrode on the user's scalp for additional comfort.

5. The EEG electrode locator headgear of claim 4, further comprising a conductive gel adapted to contact the user's scalp, said conductive gel disposed adjacent to the cushion portion of the spreader member and between the flexible, resilient fingers.

6. The EEG electrode locator headgear of claim 1, wherein said plunger assembly comprises an electrical conductor mounted to said plunger member and electrically connected between said electrically conductive spreader member and said EEG electrode locator for conducting EEG signals from said electrode to an EEG monitor.

7. The EEG electrode locator headgear of claim 1, wherein said spreader member is formed of electrically conductive silicone.

8. The EEG electrode locator headgear of claim 1, wherein said elastic, stretchable cap portion comprises at least one elastic locator strap connected to said plurality of EEG electrode locators.

9. The EEG electrode locator headgear of claim 8, wherein said at least one elastic locator strap comprises a plurality of elastic locator straps.

10. The EEG electrode locator headgear of claim 9, wherein said plurality of locator straps are made of elastic material.

11. The EEG electrode locator headgear of claim 9, wherein said plurality of locator straps are formed of elasticized fabric.

12. The EEG electrode locator headgear of claim 1, wherein said elastic, stretchable cap portion comprises a stretch mesh cap of elastic, fabric material.

13. The EEG electrode locator headgear of claim 1, further comprising an outer cap shell disposed over said elastic, stretchable cap portion.

14. The EEG electrode locator headgear of claim 13, further comprising a Faraday shield attached to the outer cap shell to provide shielding against external noise and artifacts.

15. The EEG electrode locator headgear of claim 1, wherein said base strap assembly comprises a front pad of material having first and second ends, said front pad of material being adapted to extend across a user's forehead, said base strap assembly having a first end connected to said first end of said front pad of material, and a second end connected to said second end of said front pad of material, said front pad of material and said base strap assembly being adapted to be secured comfortably around the circumference of a user's head.

16. The EEG electrode locator headgear of claim 15, further comprising a visor attached to said front pad of material.

17. The EEG electrode locator headgear of claim 1, wherein said base strap assembly is adjustable.

18. The EEG electrode locator headgear of claim 15, wherein said base strap assembly comprises a pair of adjustable elastic straps connected at one end to said front pad of material and adjustably connected together at the other end.

19. The EEG electrode locator headgear of claim 15, wherein said base strap assembly further comprises an occipital locator device adapted to be seated on a region of the user's scalp over the user's occipital bone, said base strap assembly comprising first and second elastic edge straps connected at one end to said front pad of material, and adjustably connected at the other end to said occipital locator device.

20. The EEG electrode locator headgear of claim 1, wherein said plurality of EEG electrode locators each comprise a plurality of slots for receiving at least one locator strap.

21. The EEG electrode locator headgear of claim 1, wherein each of said electrode locators comprises an electrode locator electrical conductor adapted to be electrically connected to one of said EEG electrodes inserted in said electrode locator.

22. The EEG electrode locator headgear of claim 21, wherein said electrode locator electrical conductor comprises at least one electrical contact.

23. The EEG electrode locator headgear of claim 22, wherein each of said electrode locators comprises a circuit board base member mounted to said electrode locator electrical conductor, and wherein said at least one electrical contact is connected to said circuit board base member.

24. The EEG electrode locator headgear of claim 23, wherein said plunger assembly is adapted to be received in said circuit board base member of the electrode locator.

25. The EEG electrode locator headgear of claim 24, wherein the circuit board base member includes a spring detent, and said plunger member has a plurality of grooves for engagement with the corresponding spring detent of the circuit board base member for seating the plunger assembly in the electrode locators.

26. The EEG electrode locator headgear of claim 21, further comprising circuitry to reduce noise caused by high scalp-electrode impedance electrically connected to said electrode locator electrical conductor to receive EEG signals from said electrode.

27. The EEG electrode locator headgear of claim 26, further comprising an analog to digital converter mounted on the EEG electrode locator headgear, and wherein the EEG signals from the electrode locators are conducted from said circuitry to reduce noise to the analog to digital converter.

28. The EEG electrode locator headgear of claim 27, further comprising apparatus for analyzing the digital EEG signals from the user and an RF transmitter connected to receive output from the analog to digital converter, said RF transmitter being mounted on the EEG electrode locator headgear for communicating digital EEG signals to said apparatus for analyzing the digital EEG signals from the user.

29. The EEG electrode locator headgear of claim 28, wherein said apparatus for analyzing the digital EEG signals from the user comprises a data processing unit for analyzing EEG signals from the user, and for providing feedback to the user.

30. The EEG electrode locator headgear of claim 29, wherein said data processing unit is battery powered.

31. The EEG electrode locator headgear of claim 29, wherein said data processing unit includes a speaker for transmitting audio alert messages to the user.

32. The EEG electrode locator headgear of claim 28, wherein said RF transmitter of the EEG electrode locator headgear is a bi-directional RF transmitter-receiver for receiving feedback signals from said apparatus for analyzing the digital EEG signals from the user.

33. The EEG electrode locator headgear of claim 32, further comprising a speaker mounted in the EEG electrode locator headgear for communicating audio messages from the apparatus for analyzing the digital EEG signals to the user.

34. The EEG electrode locator headgear of claim 32, further comprising storage means mounted in the EEG electrode locator headgear for storing audio messages in analog format.

35. The EEG electrode locator headgear of claim 22, wherein said plunger assembly is adapted to form an electrical connection with said at least one electrical contact.

36. The EEG electrode locator headgear of claim 1, wherein each of said electrode locators comprises a plurality of spring loaded detent pins for engagement with said electrode.

37. An electroencephalograph (EEG) electrode locator headgear, comprising:
a base strap assembly adapted to be secured comfortably around the circumference of a user's head;
an elastic, stretchable cap portion connected to said base strap assembly;
a visor connected to said base strap assembly; and
a plurality of EEG electrodes adapted to be received in said elastic, stretchable cap portion and cooperate with said elastic, stretchable cap portion.

38. The EEG electrode locator headgear of claim 37, further comprising a plurality of EEG electrode locators mounted to said elastic, stretchable cap portion for accurately positioning said plurality of EEG electrode locators relative to the user's scalp, and for biasing said plurality of electrode locators toward the user's scalp, each of said EEG electrodes including a plunger assembly adapted to seat the electrode in one of said EEG electrode locators, said plunger assembly including a plunger member having upper and lower ends, and said plunger assembly including an electrically conductive, flexible and resilient base member mounted to said lower end of said plunger member, said base member being adapted to contact the user's scalp by exertion of downward pressure of said plunger assembly against the user's scalp.

39. The EEG electrode locator headgear of claim 38, wherein said base member is tapered, and has an annular, lower end surface.

40. The EEG electrode locator headgear of claim 39, wherein said lower end surface of said base member is uneven.

41. The EEG electrode locator headgear of claim 38, wherein said base member is adapted to receive an electrically conductive gel to be pressed against the scalp.

42. The EEG electrode locator headgear of claim 38, wherein said base member is formed of electrically conductive silicone.

43. The EEG electrode locator headgear of claim 38, wherein said plurality of EEG electrode locators each comprise a plurality of slots for receiving at least one locator strap.

44. The EEG electrode locator headgear of claim 38, wherein each of said electrode locators comprises an electrode locator electrical conductor adapted to be electrically connected to one of said EEG electrodes inserted in said electrode locator.

45. The EEG electrode locator headgear of claim 44, wherein said electrode locator electrical conductor comprises at least one electrical contact.

46. The EEG electrode locator headgear of claim 45, wherein each of said electrode locators comprises a circuit board base member mounted to said electrode locator electrical conductor, and wherein said at least one electrical contact is connected to said circuit board base member.

47. The EEG electrode locator headgear of claim 46, wherein said plunger assembly is adapted to be received in said circuit board base member of the electrode locator.

48. The EEG electrode locator headgear of claim 41, wherein the circuit board base member includes a spring detent, and said plunger member has a plurality of grooves for engagement with the corresponding spring detent of the circuit board base member for seating the plunger assembly in the electrode locator.

49. The EEG electrode locator headgear of claim 46, wherein said EEG electrode locator headgear includes impedance monitoring circuitry for measuring scalp-electrode impedance values and generating impedance signals indicating said impedance values for each EEG electrode, respectively.

50. The EEG electrode locator headgear of claim 49, further comprising an analog to digital converter mounted on the EEG electrode locator headgear, wherein the impedance signals from the impedance monitoring circuitry are conducted from said impedance monitoring circuitry to said analog to digital converter.

51. The EEG electrode locator headgear of claim 45, wherein said plunger assembly is adapted to form an electrical connection with said at least one electrical contact.

52. The EEG electrode locator headgear of claim 44, further comprising circuitry to reduce noise caused by high scalp-electrode impedance electrically connected to said electrode locator electrical conductor to receive EEG signals from said electrode.

53. The EEG electrode locator headgear of claim 52, further comprising an analog to digital converter mounted on the EEG electrode locator headgear, and wherein the EEG signals from the electrode locators are conducted from said circuitry to reduce noise to the analog to digital converter mounted on the EEG electrode locator headgear.

54. The EEG electrode locator headgear of claim 53, further comprising apparatus for analyzing the digital EEG signals from the user, and an RF transmitter connected to receive output from the analog to digital converter, said RF transmitter being mounted on the EEG electrode locator headgear for communicating digital EEG signals to said apparatus for analyzing the digital EEG signals from the user.

55. The EEG electrode locator headgear of claim 54, wherein said apparatus for analyzing the digital EEG signals from the user comprises a data processing unit for analyzing EEG signals from the user, and for providing feedback to the user.

56. The EEG electrode locator headgear of claim 55, wherein said data processing unit is battery powered.

57. The EEG electrode locator headgear of claim 55, wherein said data processing unit includes a speaker for transmitting audio alert messages to the user.

58. The EEG electrode locator headgear of claim 54, wherein said RF transmitter of the EEG electrode locator headgear is a bi-directional RF transmitter-receiver for receiving feedback signals from said apparatus for analyzing the digital EEG signals from the user.

59. The EEG electrode locator headgear of claim 58, further comprising a speaker mounted in the EEG electrode locator headgear for communicating audio messages from the apparatus for analyzing the digital EEG signals to the user.

60. The EEG electrode locator headgear of claim 58, further comprising storage means mounted in the EEG electrode locator headgear for storing audio messages in analog format.

61. The EEG electrode locator headgear of claim 38, wherein each of said electrode locators comprises a plurality of spring loaded detent pins for engagement with said electrode.

62. The EEG electrode locator headgear of claim 38, wherein said plunger assembly base member is adapted to prepare the user's scalp for contact with one of said EEG electrodes.

63. The EEG electrode locator headgear of claim 38, further comprising an outer cap shell disposed over said elastic, stretchable cap portion, and a Faraday shield attached to the outer cap shell to provide shielding against external noise and artifacts.

64. The EEG electrode locator headgear of claim 37, wherein said elastic, stretchable cap portion comprises at least one elastic locator strap.

65. The EEG electrode locator headgear of claim 64, wherein said at least one elastic locator strap comprises a plurality of elastic locator straps.

66. The EEG electrode locator headgear of claim 65, wherein said plurality of locator straps are made of elastic material.

67. The EEG electrode locator headgear of claim 65, wherein said plurality of locator straps are formed of elasticized fabric.

68. The EEG electrode locator headgear of claim 37, wherein said elastic, stretchable cap portion comprises a stretch mesh cap of elastic, fabric material.

69. The EEG electrode locator headgear of claim 37, further comprising an outer cap shell disposed over said elastic, stretchable cap portion.

70. The EEG electrode locator headgear of claim 69, further comprising a Faraday shield attached to the outer cap shell to provide shielding against external noise and artifacts.

71. The EEG electrode locator headgear of claim 37, wherein said base strap assembly comprises a front pad of material having first and second ends, said front pad of material being adapted to extend across a user's forehead, said base strap assembly having a first end connected to said first end of said front pad of material, and a second end connected to said second end of said front pad of material, said front pad of material and said base strap assembly being adapted to be secured comfortably around the circumference of a user's head.

72. The EEG electrode locator headgear of claim 71, wherein said visor is attached to said front pad of material.

73. The EEG electrode locator headgear of claim 71, wherein said base strap assembly comprises a pair of adjustable elastic straps connected at one end to said front pad of material and adjustably connected together at the other end.

74. The EEG electrode locator headgear of claim 71, wherein said base strap assembly further comprises an occipital locator device adapted to be seated on a region of the user's scalp over the user's occipital bone to confirm accurate placement of the EEG electrode headgear, said base strap assembly comprising first and second elastic edge straps connected at one end to said front pad of material, and adjustably connected at the other end to said occipital locator device.

75. The EEG electrode locator headgear of claim 37, wherein said base strap assembly is adjustable.

76. The EEG electrode locator headgear of claim 37, wherein said plurality of EEG electrodes comprises two EEG electrodes.

77. The EEG electrode locator headgear of claim 37, further comprising an outer cap shell disposed over said elastic, stretchable cap portion, and a Faraday shield attached to the outer cap shell to provide shielding against external noise and artifacts.

78. The EEG electrode locator headgear of claim 37, wherein EEG electrode locator headgear includes impedance monitoring circuitry for measuring scalp-electrode impedance values and generating impedance signals indicating said impedance values for each EEG electrode, respectively.

79. An electroencephalograph (EEG) electrode locator headgear, comprising:
  a base strap assembly adapted to be secured comfortably around the circumference of a user's head, said base strap assembly including an occipital locator device adapted to be seated on a region of the user's scalp over the user's occipital bone to confirm accurate placement of the EEG electrode headgear;
  an elastic, stretchable cap portion connected to said base strap assembly; and
  a plurality of EEG electrodes adapted to be received in predetermined locations in said elastic, stretchable cap portion and cooperate with said elastic, stretchable cap portion.

80. The EEG electrode locator headgear of claim 79, further comprising an outer cap shell disposed over said elastic, stretchable cap portion, and a Faraday shield attached to the outer cap shell to provide shielding against external noise and artifacts.

81. The EEG electrode locator headgear of claim 79, wherein EEG electrode locator headgear includes impedance monitoring circuitry for measuring scalp-electrode impedance values and generating impedance signals indicating said impedance values for each EEG electrode, respectively.

82. An improvement in a portable electroencephalograph (EEG) electrode locator headgear, the EEG electrode locator headgear including a base strap assembly adapted to be secured comfortably around the circumference of a user's head, an elastic, stretchable cap portion connected to said base strap assembly, a visor connected to said base strap assembly, a plurality of EEG electrodes adapted to be received in predetermined locations in said elastic, stretchable cap portion and cooperate with said elastic, stretchable cap portion, and an outer cap shell disposed over said elastic, stretchable cap portion, the improvement comprising a Faraday shield attached to the outer cap shell to provide shielding against external noise and artifacts.

83. All improvement in a portable electroencephalograph (EEG) electrode locator headgear, the EEG electrode locator headgear including a base strap assembly adapted to be secured comfortably around the circumference of a user's head, an elastic, stretchable cap portion connected to said base strap assembly, a visor connected to said base strap assembly, a plurality of EEG electrodes adapted to be received in predetermined locations in said elastic, stretchable cap portion and cooperate with said elastic, stretchable cap portion, the improvement comprising impedance monitoring circuitry associated with said plurality of EEG electrodes for measuring scalp-electrode impedance values and generating impedance signals indicating said impedance values for each EEG electrode, respectively.

* * * * *

UNITED STATES PATENT AND TRADEMARK OFFICE
CERTIFICATE OF CORRECTION

PATENT NO. : 6,381,481 B1  
DATED : April 30, 2002  
INVENTOR(S) : Daniel J. Lenendowski et al.

It is certified that error appears in the above-identified patent and that said Letters Patent is hereby corrected as shown below:

Column 6,  
Line 67, change "locations", to read -- locators --.

Column 23,  
Line 10, change "All", to read -- An --

Signed and Sealed this

Twenty-fifth Day of June, 2002

Attest:

Attesting Officer

JAMES E. ROGAN  
Director of the United States Patent and Trademark Office

UNITED STATES PATENT AND TRADEMARK OFFICE
CERTIFICATE OF CORRECTION

PATENT NO. : 6,381,481 B1  
DATED : April 30, 2002  
INVENTOR(S) : Levendowski, D.

It is certified that error appears in the above-identified patent and that said Letters Patent is hereby corrected as shown below:

Title page,
Item [56], References Cited, OTHER PUBLICATIONS, replace the item with:
-- Article entitled "A Dry Electrode For EEG Recording", B. Taheri, R. Knight, and R. Smith, 1994 Elsevier Science Ireland Ltd. pp.2-9. --

Column 20,
Lines 33-38, please replace claim 48 with the following claim:

48.  The EEG electrode locator headgear of claim 47, wherein the circuit board base member includes a spring detent, and said plunger member has a plurality of grooves for engagement with the corresponding spring detent of the circuit board base member for seating the plunger assembly in the electrode locator.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.         : 6,381,481 B1                                     Page 1 of 1
APPLICATION NO. : 09/492380
DATED              : April 30, 2002
INVENTOR(S)        : Daniel J. Levendowski et al.

It is certified that error appears in the above-identified patent and that said Letters Patent is hereby corrected as shown below:

Column 1, lines 9-14, delete "The United States Government has rights to this invention pursuant to research supported in the whole or in part by NIH Contracts R43-NS-62344, N43-NS-72367 and N44-NS-72367 and grants R43-NS-35387, R44-NS-35387 and R44-NS38036 awarded by the National Institute of Neurological Disorders and Stroke." and insert instead --This invention was made with government support under NIH contracts N43-NS-62344, N43-NS-72367 and N44-NS-72367 and grants R43-NS-35387, R44-NS-35387 and R44-NS38036 awarded by the National Institute of Neurological Disorders and Stroke. The government has certain rights in the invention.--

Signed and Sealed this

Fifteenth Day of June, 2010

David J. Kappos
*Director of the United States Patent and Trademark Office*